US009504491B2

(12) United States Patent
Callas et al.

(10) Patent No.: US 9,504,491 B2
(45) Date of Patent: Nov. 29, 2016

(54) CATHETER HAVING WINDOW AND PARTIAL BALLOON COVERING FOR DISSECTING TISSUE PLANES AND INJECTING TREATMENT AGENT TO CORONARY BLOOD VESSEL

(75) Inventors: Peter L. Callas, Castro Valley, CA (US); Eric J. Willis, Santa Cruz, CA (US); Fozan O. El-Nounou, Santa Clara, CA (US); Florian N. Ludwig, Mountain View, CA (US); William E. Webler, San Jose, CA (US); Paul M. Consigny, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 777 days.

(21) Appl. No.: 11/936,668

(22) Filed: Nov. 7, 2007

(65) Prior Publication Data
US 2009/0118700 A1    May 7, 2009

(51) Int. Cl.
| | | |
|---|---|---|
| *A61B 17/34* | (2006.01) | |
| *A61M 25/10* | (2013.01) | |
| *A61B 17/02* | (2006.01) | |
| *A61B 17/00* | (2006.01) | |
| *A61B 17/22* | (2006.01) | |
| *A61B 17/32* | (2006.01) | |

(Continued)

(52) U.S. Cl.
CPC .......... *A61B 17/3478* (2013.01); *A61M 25/10* (2013.01); *A61B 17/02* (2013.01); *A61B 90/37* (2016.02); *A61B 2017/00247* (2013.01); *A61B 2017/22061* (2013.01); *A61B 2017/320044* (2013.01); *A61B 2018/00392* (2013.01); *A61M 25/0026* (2013.01); *A61M 25/0084* (2013.01); *A61M 2025/0166* (2013.01); *A61M 2025/1004* (2013.01)

(58) Field of Classification Search
CPC ............ A61M 2025/0086; A61M 2025/0087; A61M 2025/0085; A61M 2025/009; A61M 3/0295
USPC ............. 604/506, 507, 522, 164.01; 600/439
See application file for complete search history.

(56) References Cited

U.S. PATENT DOCUMENTS

| | | |
|---|---|---|
| 4,177,818 A | 12/1979 | De Pedro |
| 4,323,081 A | 4/1982 | Wiebusch |

(Continued)

OTHER PUBLICATIONS

PCT International Search Report and Written Opinion for PCT International Appln No. PCT/US2008/012597, mailed on Feb. 10, 2009 (13 pages).

(Continued)

*Primary Examiner* — Bhisma Mehta
*Assistant Examiner* — Matthew A Engel
(74) *Attorney, Agent, or Firm* — Blakely Sokoloff Taylor & Zafman LLP

(57) ABSTRACT

A method is provided including introducing a delivery device through a vessel wall to a treatment site within one of a peri-adventitial space or a pericardium adjacent a coronary blood vessel and delivering a treatment agent through the delivery device. The treatment agent is delivered through the delivery device according to conditions that hydraulically dissect tissue planes within the peri-adventitial space. A kit is provided including a delivery device having a needle to be advanced through one of an epicardium of a heart and a wall of a coronary blood vessel into a peri-adventitial space and a treatment agent comprising particles having an average diameter on the order of 15 microns or more to be delivered through the delivery device into the peri-adventitial space.

11 Claims, 11 Drawing Sheets

(51) Int. Cl.
*A61B 18/00* (2006.01)
*A61M 25/00* (2006.01)
*A61M 25/01* (2006.01)

(56) References Cited

U.S. PATENT DOCUMENTS

| | | | |
|---|---|---|---|
| 4,402,685 A * | 9/1983 | Buhler et al. | 604/523 |
| 4,694,838 A * | 9/1987 | Wijayarthna et al. | 600/435 |
| 4,769,005 A * | 9/1988 | Ginsburg et al. | 604/510 |
| 5,022,414 A | 6/1991 | Muller | 128/898 |
| 5,088,991 A * | 2/1992 | Weldon | 604/523 |
| 5,112,299 A | 5/1992 | Pascaloff | |
| 5,195,962 A * | 3/1993 | Martin et al. | 604/43 |
| 5,489,278 A * | 2/1996 | Abrahamson | 604/523 |
| 5,538,504 A * | 7/1996 | Linden et al. | 604/508 |
| 5,609,574 A * | 3/1997 | Kaplan et al. | 604/508 |
| 5,653,690 A | 8/1997 | Booth et al. | |
| 5,810,809 A | 9/1998 | Rydell | |
| 5,827,229 A * | 10/1998 | Auth et al. | 604/171 |
| 5,865,748 A | 2/1999 | Co et al. | |
| 6,027,461 A * | 2/2000 | Walker et al. | 600/585 |
| 6,179,828 B1 * | 1/2001 | Mottola et al. | 604/523 |
| 6,428,539 B1 | 8/2002 | Baxter et al. | |
| 6,447,525 B2 | 9/2002 | Follmer et al. | |
| 6,585,694 B1 | 7/2003 | Smith et al. | |
| 6,623,733 B1 * | 9/2003 | Hossainy et al. | 424/93.21 |
| 6,638,233 B2 | 10/2003 | Corvi et al. | |
| 6,692,466 B1 | 2/2004 | Chow et al. | |
| 6,702,744 B2 | 3/2004 | Mandrusov et al. | |
| 6,759,431 B2 | 7/2004 | Hunter et al. | |
| 7,008,411 B1 | 3/2006 | Mandrusov et al. | |
| 7,357,794 B2 * | 4/2008 | Makower et al. | 604/500 |
| 2001/0007059 A1 | 7/2001 | Mirzaee | |
| 2002/0002349 A1 * | 1/2002 | Flaherty et al. | 604/164.11 |
| 2003/0021848 A1 | 1/2003 | Johnson et al. | |
| 2003/0040712 A1 | 2/2003 | Ray et al. | |
| 2003/0149368 A1 * | 8/2003 | Hennemann et al. | 600/483 |
| 2003/0171734 A1 | 9/2003 | Seward et al. | |
| 2004/0015193 A1 * | 1/2004 | Lamson et al. | 607/9 |
| 2004/0138562 A1 * | 7/2004 | Makower et al. | 600/439 |
| 2004/0162516 A1 | 8/2004 | Mandrusov et al. | |
| 2005/0084515 A1 | 4/2005 | Udipi et al. | |
| 2005/0197633 A1 * | 9/2005 | Schwartz et al. | 604/264 |
| 2006/0106338 A1 | 5/2006 | Chang | |
| 2006/0135943 A1 * | 6/2006 | Mandrusov et al. | 604/500 |
| 2007/0010793 A1 | 1/2007 | Callas et al. | |
| 2007/0038173 A1 | 2/2007 | Simpson | |
| 2007/0093779 A1 | 4/2007 | Kugler et al. | |
| 2008/0058759 A1 * | 3/2008 | Makower et al. | 604/509 |
| 2009/0118700 A1 * | 5/2009 | Callas et al. | 604/508 |

OTHER PUBLICATIONS

Cheneau, Edouard, et al., "Impact of Sirolimus-Eluting Stents on Outcomes of Patients Treated for Acute Myocardial Infarction by Primary Angioplasty," Catherterization and Cardiovascular Interventions, 2005, pp. 469-472, 65.

Costantini, Costantino O., et al., "Frequency, Correlates, and Clinical Implications of Myocardial Perfusion After Primary Angioplasty and Stenting, With and Without Glycoprotein IIb/IIIa Inhibition, in Acute Myocardial Infarction," Journal of the American College of Cardiology, Jul. 21, 2003, pp. 305-312, 44(2).

Halkin, Amir, et al., "Prediction of Morality After Primary Percutaneous Coronary Intervention for Acute Myocardial Infarction," Journal of the American College of Cardiology, May 3, 2005, pp. 1397-1405, 45(9).

Kandzari, David E., et al., "Comparison of Long-Term (Seven Year) Outcomes Among Patients Undegoing Percutaneous Coronary REvascluarization With Versus Without Stenting," The American Journal of Cardiology, 2006, pp. 1467-1472.

Mandrusov, Evgenia et al., "Agents That Stimulate Therapeutic Angiogenesis and/or Angiomygenesis and Techniques and Devices That Enable Delivery," U.S. Appl. No. 10/792,960, filed Mar. 3, 2004.

Mehta, Rajendra H., et al., "Clinical and Angiographic Correlates and Outcomes of Suboptimal Coronary Flow in Patients With Acute Myocardial Infarction Undergoing Primary Percutaneous Coronary Intervention," Journal of the American College of Cardiology, Nov. 19, 2003, pp. 1739-1746, 42(10).

Mehta, Rajendra H., et al., "Comparison of Coronary Stenting Versus Conventional Balloon Angioplasty on Five-Year Mortality in Patients With Acute Myocardial Infarction Undergoing Primary Percutaneous coronary Intervention," The American Journal of Cardiology, 2005, pp. 901-906.

Abbott Cardiovascular Systems, International Preliminary Report on Patentability dated May 11, 2010 for PCT/US2008/012597.

* cited by examiner

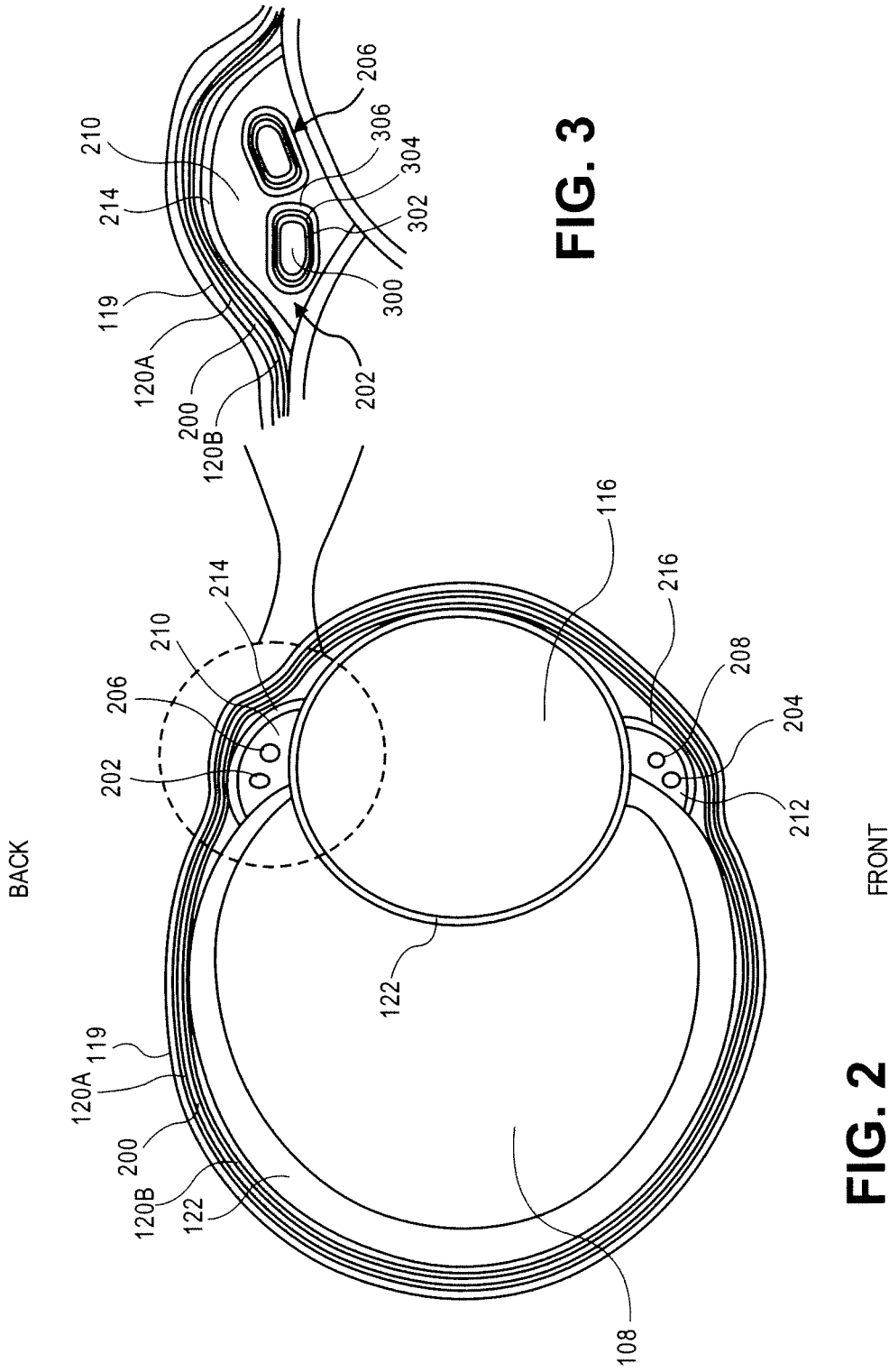

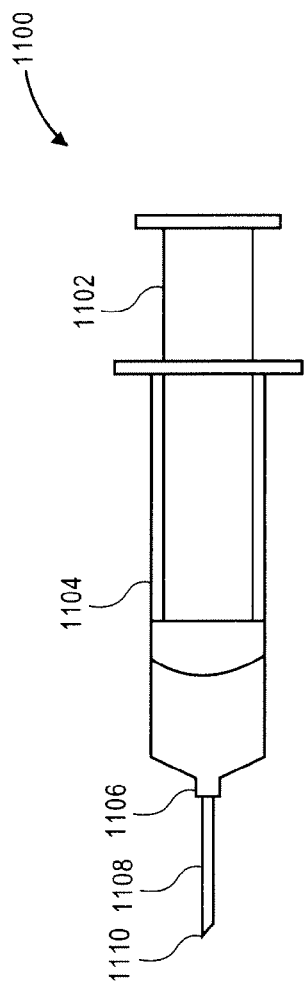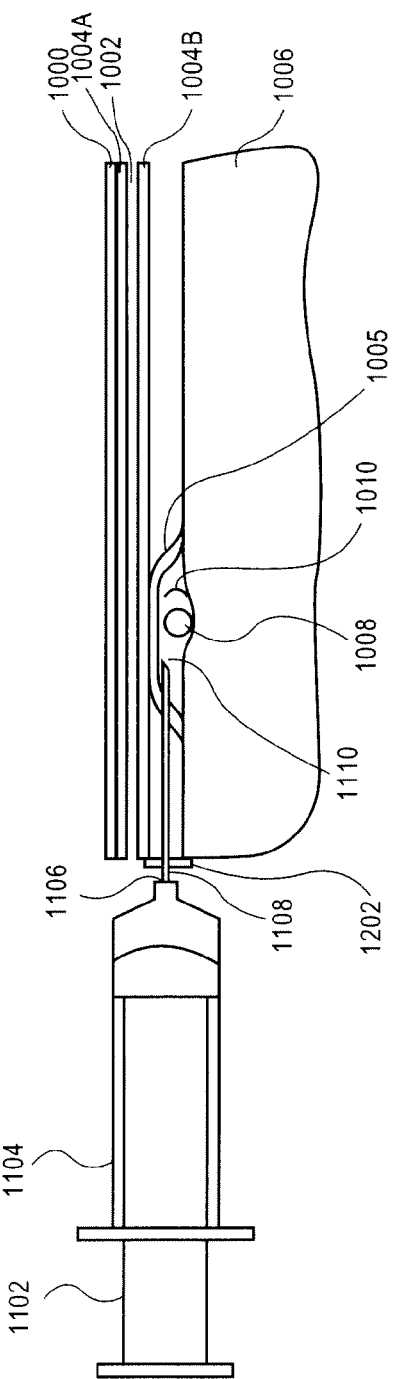

CATHETER HAVING WINDOW AND PARTIAL BALLOON COVERING FOR DISSECTING TISSUE PLANES AND INJECTING TREATMENT AGENT TO CORONARY BLOOD VESSEL

BACKGROUND

Field

Methods for delivering treatment agents to coronary vessels. In particular, methods and kits for delivering treatment agents to tissues or spaces adjacent to coronary vessels.

Background

Cardiovascular diseases of the heart or blood vessels continue to affect individuals within the United States and many Western countries at increasingly alarming rates. A major component of morbidity and mortality attributable to cardiovascular disease occurs as a consequence of the partial or complete blockage of vessels carrying blood in the coronary and/or peripheral vasculature caused by diseased vessels. When such vessels are partially occluded, lack of blood flow causes ischemia of the muscle tissues supplied by such vessel, consequently inhibiting muscle contraction and proper function. Total occlusion of blood flow causes necrosis of the vasculature and muscle tissues.

Myocardial infarction (MI) is one form of heart disease that often results from the sudden lack of supply of oxygen and other nutrients. The lack of blood supply is a result of closure of the coronary artery that nourishes a particular part of the heart muscle. The cause of this event is generally attributed to arteriosclerosis, "hardening of the arteries", in coronary vessels.

Formerly, it was believed that an MI was caused from a slow procession of closure from, for example, 95 percent then to 100 percent but an MI can also be a result of minor blockages where, for example, there is rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Blood vessel stenosis or occlusions are commonly treated by mechanically enhancing blood flow in the affected vessels. Such mechanical enhancements often employ surgical techniques that attach natural or synthetic conduits around the occlusion, thereby providing bypass grafts, or employ revascularization by various means to physically enlarge the vascular lumen at the site of occlusion. These revascularization procedures involve balloons, endovascular knives (atherectomy), and endovascular drills. Significant morbidity and even mortality frequently accompany surgical approaches, while, in many cases, recurrent stenoses complicate angioplasty-type processes.

Systemic, local or direct drug delivery techniques designed to treat damaged heart and vasculature tissues may accompany or replace mechanical techniques. Such techniques, however, can be problematic for a number of reasons. In particular, in systemic delivery techniques, the whole organism is treated therefore greater amounts of drugs must be supplied which are sometimes toxic to the organism. In local delivery techniques the therapeutic is typically injected into a blood stream at a point upstream from the treatment site or into an unperfused vessel region after first occluding the vessel region to inhibit blood flow. In either case, once blood flow is restored, as it must be to prevent further damage to the vessel, the therapeutic is washed away from the region where delivery is desired. Lastly, in direct delivery, typically, the drug is delivered through a vessel wall into dense tissues having few spaces for accommodating fluid uptake. Accordingly, administering an effective drug amount may require several injections to the region.

SUMMARY

A method is disclosed. In one embodiment the method includes introducing a delivery device to a treatment site within a peri-adventitial space surrounding a coronary blood vessel. At least 1.0 cubic centimeters (cc) of a treatment agent may be delivered through the delivery device to a region of the peri-adventitial space according to conditions that hydraulically dissect tissue planes within the peri-adventitial space. The term "hydraulic dissection" as used herein refers to the separation of tissue planes by delivering a fluid to a tissue at a pressure or flow rate sufficient to separate the tissue planes and create repositories between the tissue planes for accommodating a substance. The delivery device may be introduced to the treatment site by positioning the delivery device within a blood vessel and advancing the delivery device needle through a vessel wall. Alternatively, the delivery device may be introduced to the peri-adventitial space by positioning the delivery device adjacent the pericardium and advancing a delivery device needle through the pericardium and into the epicardium. The delivery conditions that hydraulically dissect tissue planes include delivering the treatment agent into the peri-adventitial space at a pressure or flow rate that creates a repository between the tissue planes for accommodating the treatment agent.

In another embodiment, a method includes introducing a delivery device to a site within a peri-adventitial space surrounding a coronary blood vessel. Tissue planes within the peri-adventitial space are hydraulically dissected by delivering the solution to the peri-adventitial space through the delivery device according to conditions that hydraulically dissect tissue planes within the space. Saline is a suitable solution. Applying negative pressure to the delivery device allows the solution to drain from the peri-adventitial space. After draining the solution, a treatment agent may be delivered into the peri-adventitial space through the device. Between 0.1 and 20 cc of treatment agent may be delivered into this space.

In another embodiment, a method includes introducing a delivery device to a treatment site within a peri-adventitial space surrounding a coronary blood vessel through an epicardial layer. A treatment agent is delivered through the delivery device under conditions that hydraulically dissect tissue planes within the peri-adventitial space.

Still another embodiment features a kit including a delivery device comprising a needle to be advanced through one of an epicardium of a heart or a wall of a coronary blood vessel into a peri-adventitial space. The kit further includes a treatment agent to be delivered into the peri-adventitial space through the delivery device. The treatment agent comprises particles having an average diameter on the order of 15 microns or more.

Other embodiments feature methods for introducing a delivery device to a treatment site within one of a peri-adventitial space or a pericardium adjacent a coronary blood vessel. The method further includes delivering a controlled release treatment agent at the treatment site.

As used herein, treatment agents include, but are not intended to be limited to, drugs, biologically active agents, chemically active agents, therapeutic agents, and the like, and pharmaceutical compositions thereof, which can be used to deliver a treatment agent to a treatment site as described herein. In some embodiments, the treatment agent may be an agent suitable for local treatment, regional treatment or a combination of agents suitable for local and regional treatment.

In some embodiments, the treatment agent may be a drug including, but not limited to, a high density lipoprotein (HDL) mimetic, an anti-inflammatory and an anti-proliferative. Alternatively, the treatment agent may be a non-living biologic including, but not limited to, an extra cellular matrix, urinary bladder matrix, small intestinal submucosa or a liver derived biomatrix. Still further, the treatment agent may be a living biologic including, but not limited to, bone marrow stem cells, mesenchymal cells and endothelial progenitor cells.

Treatment agent delivery can be solution-based, such as a microparticle or nanoparticle within a carrier. The carrier can include a property to control a release rate of the treatment agent. In other embodiments, the treatment agent may be within a gel.

BRIEF DESCRIPTION OF THE DRAWINGS

FIG. 2 schematically illustrates a cross-section of the heart.

FIG. 3 schematically illustrates a magnified view of a region of the heart illustrated in FIG. 2.

FIG. 11 schematically illustrates an embodiment of a direct access system.

FIG. 12 schematically illustrates another embodiment of a direct access system.

DETAILED DESCRIPTION

The following description provides for techniques for locally treating regions of a blood vessel by delivering a treatment agent to a region adjacent the vessel. For example, in some embodiments, the treatment agent is delivered to a peri-adventitial space surrounding a coronary blood vessel. In some embodiments, the peri-adventitial space is hydraulically dissected during or prior to delivery of the treatment agent. The term "peri-adventitial space" as used herein refers to an anatomical confluence of tissue planes surrounding a blood vessel that are between an adventitial layer of the blood vessel wall and a fat layer overlying the blood vessel. As previously discussed, the term "hydraulic dissection" as used herein refers to the separation of tissue planes by delivering a fluid to the tissue at a pressure or flow rate sufficient to separate the tissue planes and create repositories between the tissue planes for accommodating a substance. Various devices are described herein for hydraulically dissecting the tissue planes and delivering the treatment agent. But other devices known in the art may be used.

Alternatively, a coronary vessel may be treated by delivering a treatment agent to a region of a pericardium surrounding a heart and the blood vessels. In some embodiments, the treatment agent is delivered to a pericardial cavity having serous fluid therein. In other embodiments, the treatment agent is delivered to tissues of the pericardium.

Figure 1:
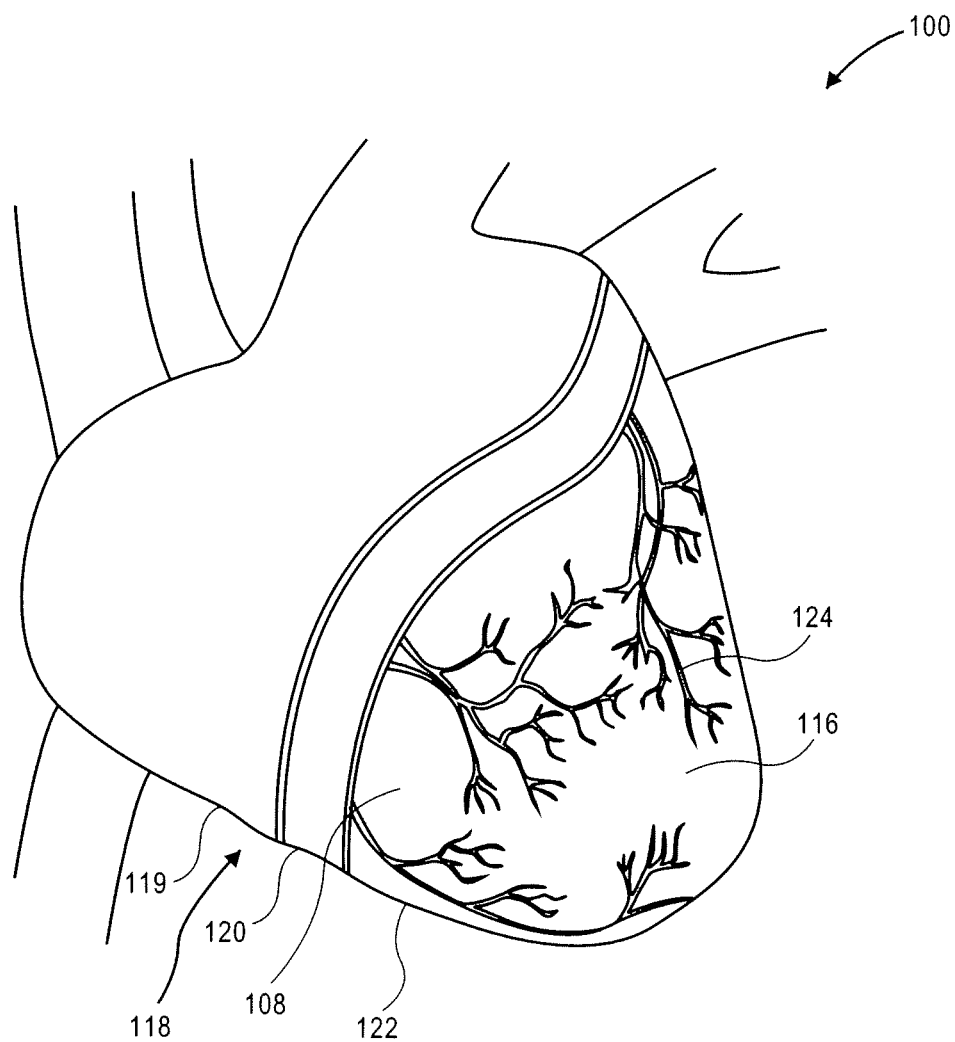
FIG. 1 schematically illustrates vasculature and tissue layers overlying a heart.

Referring to FIG. 1, a simplistic view of a heart is shown to illustrate the vasculature and tissue layers enveloping it. Heart 100 includes various chambers, valves (not shown) and vessels for pumping and transporting blood throughout the body. A pericardium 118 envelopes heart 100. Pericardium 118 is a multilayered sack having a superficial fibrous layer 119 and a deeper serous layer 120. Serous layer 120 has a parietal layer 120A and a visceral layer 120B (see FIG. 2). Visceral layer 120B is the epicardium. A pericardial space or cavity which contains serous or pericardial fluid lies between parietal layer 120A and epicardium 120B. Epicardium 120B contacts myocardium 122 on the side opposite the pericardial space. Blood vessels 124 lie between serous layer 120 and myocardium 122.

Blood vessels 124 are coronary arteries and veins surrounding heart 100. About 10 centimeters (cm) to 15 cm of blood vessels 124 are exposed around the outer surface of heart 100 and beneath pericardium 118. Coronary arteries have their walls fed by vasa vasorum. The vasa vasorum is a network of small arteries and veins that run roughly parallel to and down the outer surface of the artery with small branches around the artery that penetrate the artery wall. In arteries with plaques, especially metabolically active plaques like vulnerable plaques, growing plaques or plaques in the process of becoming vulnerable, the vasa vasorum grows larger and grows many more small feeding and branching arteries into the coronary artery wall and into the plaques themselves to support the increased metabolic activity. Treatment agents delivered and released within the pericardium (e.g. the pericardial space) and its adjacent regions (e.g., peri-advential space) will have a higher concentration in the vicinity of the vasa vasorum than that which would be found in the blood if the agent were delivered systemically or locally. It is, however, recognized that this concentration difference may vary depending upon factors of the treatment solution such as the clearance rate, the amount of the treatment agent and dissolution rate of the treatment agent. The high agent concentration outside the vasa vasorum will drive the treatment agent across the thin walls of the arteries of the vasa vasorum thereby feeding the plaques and transporting the treatment agent directly into the environment inside the plaque. The concentration difference will also drive the treatment agent into the coronary arterial blood via the arterial wall (i.e., via the vasa vasorum vessels) feeding other tissues of the heart. In this aspect, the tissues of the heart will be exposed to greater than systemic concentrations of the treatment agents. Thus, in the case of potent treatment agents with undesired systemic side effects, the concentration of the treatment agent may be kept at effective levels for the desired time of treatment in a target tissue of the heart, but at a low level systemically thereby limiting undesired systemic effects. Additionally the total amount of the treatment agent required will be less than that which would be required if applied using a systemic dosing method. This may be a benefit where the cost of the treatment agent is high. In addition, applying the treatment agent in a time release manner in the peri-adventitial space or pericardium assures the effective application of the treatment agent and doesn't rely on the often unreliable compliance of the patient.

FIG. 2 illustrates a cross-section of heart 100 illustrated in FIG. 1. FIG. 2 shows a right ventricle 108 and a left ventricle 116 bounded by myocardium 122. Overlying myocardium 122 is epicardium 120B, which is further enveloped by parietal layer 120A and fibrous layer 119. The figure illustrates pericardial space 200 between parietal layer 120A and epicardium 120B. Positioned along a back side of heart 100 are artery 202 and vein 206, which are within peri-adventitial space 210. Myocardium 122 and fat layer 214 bound peri-adventitial space 210. Similarly, artery 204 and vein 208 lie along a front side of heart 100. Artery 204 and vein 208 are within peri-adventitial space 212 which is bounded by myocardium 122 and a fat layer 216.

Peri-adventitial space 210, 212 is an anatomical confluence of tissue planes surrounding coronary blood vessels. As is apparent from the enlarged view of this region illustrated in FIG. 3, peri-adventitial space 210, 212 refers to a region separate from the tissue layers making up the walls of the blood vessels. This aspect is illustrated in FIG. 3 with respect to artery 202. Artery 202 includes an arterial wall having a number of layers extending outwardly from lumen 300. Innermost layer 302 represents the intimal layer that includes the endothelium, the subendothelial layer, and the internal elastic lamina. Medial layer 304 is concentrically outward from intimal layer 302 and bounded by external elastic lamina and an outermost adventitial layer 306. There is no external elastic lamina in a vein. Medial layer 304 (in either an artery or vein) primarily consists of smooth muscle fibers and collagen. Beyond medial layer 304 and adventitial layer 306 lies the peri-adventitial space 210. Areas radially outward from peri-adventitial space 210 include connective tissue, such as adipose tissue that is most likely located, in terms of areas around the heart, toward the epicardial surface of the heart, and myocardial tissue composed of muscle fibers.

Figure 4:
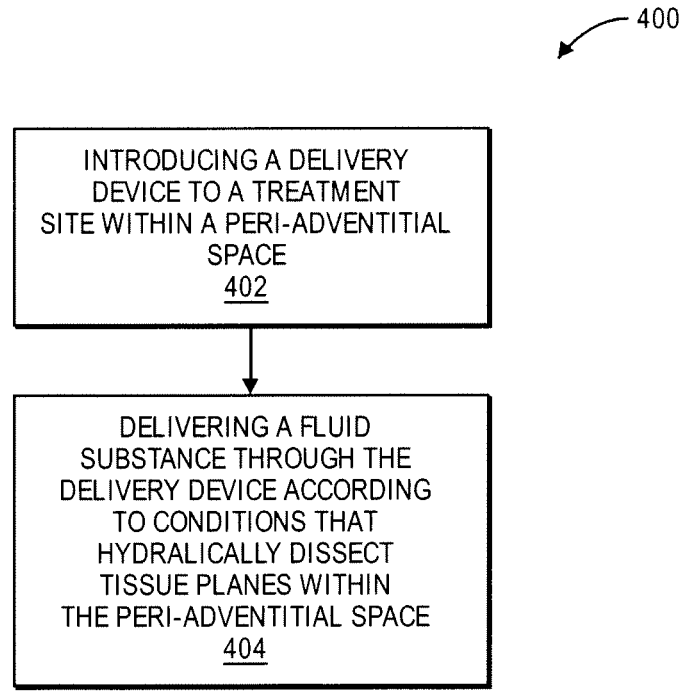
FIG. 4 is a flowchart detailing a method for delivering a treatment agent to a peri-adventitial space using a delivery device.

FIG. 4 is a flowchart detailing a method 400 for delivering a fluid substance to the peri-adventitial space using a delivery device. In one embodiment, a delivery device is introduced to a treatment site within a peri-adventitial space (block 402). In one embodiment, the delivery device may be introduced to the treatment site by positioning the delivery device within a blood vessel lumen and advancing the device through a wall of the blood vessel. In this aspect, the device may include an assembly, for example, a needle, to pierce through the vessel wall and into the peri-adventitial space.

Alternatively, the delivery device may be introduced to the treatment site via a route outside of the blood vessel. In one embodiment, the delivery device may be introduced through the chest by, for example, a subxiphoid, sub-sternal or thoracascopic insertion route, and maneuvered to a region of the heart adjacent the treatment site. In another embodiment, the delivery device may be introduced directly to an exposed region of the heart. This technique may be particularly desirable, for example, where the patient is undergoing cardiac surgery and therefore their chest cavity is opened exposing the heart. Once in position, a needle, for example, of the delivery device, may be advanced through the various layers overlying the peri-adventitial space and into the tissues within this region. In still further embodiments, the delivery device may be introduced to the treatment site through the heart. For example, the delivery device may be advanced through a vessel terminating within the heart. A needle of the delivery device is then advanced through a wall of the heart to the desired treatment site, for example, the peri-adventitial space.

In some embodiments, the above described techniques are further used to introduce the delivery device into tissue regions of the pericardium enveloping the heart. For example, where the delivery device is positioned within a vessel, the device needle is advanced through the vessel wall, the peri-adventitial space and the epicardium until an outlet port of the needle is within the pericardial cavity. Accordingly, although delivery of the treatment agent to the peri-adventitial space using the techniques and devices referenced herein are described, it is further contemplated that the techniques and devices may further be used to introduce the treatment agent to tissues or spaces within the pericardium.

In some embodiments, a guidance device is used to position the delivery device within a desired treatment region. In some embodiments, the guidance device is a conventional imaging modality capable of allowing for visualization of the tissue layers or delivery device as the needle is advanced to the desired treatment region. Representative imaging modalities include optical coherence tomography, fiberoptic, ultrasonic, x-ray or magnetic resonance based imaging systems that image the tissue and/or the needle. For example, in the case of an ultrasonic imaging modality, a pointed (distal) end of the device needle is visualized during advancement through the tissue layers.

Where the needle is positioned within the peri-adventitial space, a fluid substance may be delivered through the delivery device according to conditions that hydraulically dissect tissue planes within the peri-adventitial space (block 404). In their natural anatomical configuration, tissue planes of the peri-adventitial space are relatively compact without spaces and channels between them for fluid retention. For this reason, typically an effective volume amount of a fluid such as a treatment agent for treating a target region may not be accommodated within the peri-adventitial space. Moreover, since there are no spaces and channels between the tissue planes, there is only minimal diffusion of any fluids within the peri-adventital space to tissue regions outside of the delivery point. Accordingly, if before or during delivery of a treatment agent the tissue planes become hydraulically dissected, larger volumes of the agent may be delivered to the site. In addition, the spaces between the planes allow the treatment agent to diffuse throughout a greater tissue region than when the tissues are not hydraulically dissected.

In one embodiment, a pressure sufficient to separate the tissue planes may be between approximately 30 mm Hg and 1000 mm Hg. In another embodiment, the pressure sufficient to separate the tissue planes may be between approximately 80 mm Hg and 200 mm Hg. Still further, the pressure sufficient to separate the tissue planes may be approximately 150 mm Hg. In one embodiment, a volumetric flow rate sufficient to separate tissue planes may be that which is less than a flow rate which disrupts or kills cells. In this aspect, a fluid may be delivered to the peri-adventitial space at a pressure and volumetric flow rate which keeps the fluid below a level that disrupts or kills cells.

A fluid volume suitable for hydraulically dissecting tissue planes within, for example, the peri-adventitial space may be at least 1.0 cc. It is recognized that due to the compact tissue layers of the peri-adventitial space, some of the fluid used for dissection of the space is lost around a delivery needle. Accordingly, in embodiments where the treatment agent is used as the fluid for hydraulically dissecting the tissue planes, generally, a higher fluid volume than that which is needed to effectively treat the desired region is delivered. In embodiments where the treatment agent is delivered after hydraulic dissection of the peri-adventitial space, a lower fluid volume that that which is needed for dissection of the tissue may be delivered.

Delivery of a treatment agent to a hydraulically dissected peri-adventitial space or pericardial cavity as described herein may be useful in treating various cardiovascular diseases and in particular conditions affecting coronary arteries such as hyperplasia or vulnerable plaque. In addition, the methods described herein, may further be useful in regional therapies, cellular therapies and diffuse diseases. In particular, spaces between dissected tissues of the peri-adventitial space or within the pericardium serve as repositories for the treatment agent. Accordingly, the treatment agent is not washed away from the treatment site as is common in, for example, local delivery methods. Instead, the agents diffuse throughout the tissue spaces of, for example, the peri-adventitial space longitudinally along the underlying vessel walls. In addition, some of the treatment agent may diffuse through the fat layer overlying the vessel and peri-adventitial space and diffuse along the vessel wall. The treatment agent thus remains along the vessel and, over time, diffuses through the layers of the vessel wall treating the diseased or damaged vessel region.

Any suitable biocompatible substance or solution may be used to hydraulically dissect tissue planes of the peri-adventitial space. In some embodiments, a suitable solution may be a saline solution or a solution including a treatment agent. In this aspect, a volume of the solution (e.g., saline or treatment agent solution) may be delivered to the peri-adventitial space at a sufficient pressure or volumetric flow rate to dissect the tissue planes within the peri-adventitial space. In one embodiment, the solution may be delivered at a pressure or volumetric flow rate as previously discussed with respect to the treatment agent. In one embodiment, the solution may be delivered at a high pressure of least about 300 mm Hg. Once dissection of the tissue is achieved, in the case of a saline solution, the saline may be withdrawn from the tissue by applying a negative pressure. The tissue planes remain separated for a period of time before re-adhering to each other. During this period, a volume of the treatment agent may be delivered to the tissue. Representative volumes of treatment agent delivered to the tissue may be, for example, between 0.1 cc and 20 cc, and in some embodiments between 0.1 cc to 5 cc or between 0.1 cc to 0.2 cc.

The treatment agent may be any agent suitable for treating coronary vessel tissues and cardiac ailments. For example, in one embodiment, the treatment agent treats the progression of atherosclerosis. Representative atherosclerotic treatment agents include anti-inflammatory, statin, cholesterol acceptor and antioxidant agents. In other embodiments, the treatment agent treats coronary vascular dysfunction. Representative coronary vascular dysfunction treatment agents include nitric oxide donors or generators and adiponectin agents. Still further, the treatment agent treats fractures or thrombosis of vulnerable lesions. Representative vulnerable lesion treatment agents include inhibitors of tissue factor and metalloproteinase inhibitors. The treatment agent may further treat pericarditis, arrhythmia or cardiac metastases. Representative pericarditis, arrhythmia and cardiac metastases treatment agents include antibiotics, anti-arrhythmic and chemotherapeutic agents, respectively.

In one embodiment, the treatment agent may be a drug. Representative drugs include HDL mimetics, anti-inflammatory agents and anti-proliferative agents. Exemplary HDL mimetics include cyclodextrin. Exemplary anti-inflammatory agents include clobetasol, dexamethasone, prednisone, aspirin and cortisone. Exemplary anti-proliferative agents include taxol, everolomus, sirolomus, doxorubicin and other chemotherapeutic agents. Still further representative drugs include apolipoprotein A1 (APO A1).

In one embodiment, the treatment agent may be a non-living biologic. In one embodiment, the non-living biologic may include scaffolding such as an Extra Cellular Matrix (ECM). Representative non-living biologics may include Urinary Bladder Matrix (UBM), Small Intestinal Submucosa (SIS) and liver derived BioMatrix (LBM).

In another embodiment, the treatment agent may be a living biologic. The peri-adventitial space is particularly suitable for delivering living biologics. Representative living biologics include bone marrow stem cells, mesenchymal cells and endothelial progenitor cells.

In one embodiment, one or more of the above described agents can be encapsulated, suspended, disposed within or loaded into a biodegradable carrier. Examples of biodegradable carriers include, but are not limited to, a liposome, a polymerosome, a micelle, a particle and a gel. Examples of particles include, but are not limited to, microparticles and nanoparticles. In some embodiments, the biodegradable carrier is formulated such that it is bioerodable when present in physiological conditions.

In one embodiment, the biodegradable carrier for the treatment agent is a liposome. A "Liposome" is an artificial vesicle that is approximately spherical in shape and can be produced from natural phospholipids and cholesterol. In one method, phospholipids are mixed with cholesterol in chloroform. Suitable phospholipids include, but are not limited to, dimyristoyl phosphatidyl choline (DMPC) or dipalmitoyl ethanolamine. For hydrophobic treatment agents, the treatment agent can be added with an optional co-solvent, such as heptane or toluene. The liposomes can also be hydrophilically modified with an agent such as polyethylene glycol or dextran. After mixing, the solvent (and optional co-solvent) can be evaporated with heat or ambient temperature in a round bottom flask. Resultant lipids will be deposited on the glass surface. The deposited lipid film will be re-suspended in aqueous solution to form multilamellar vesicles, and extruded to prepare appropriate sized liposomes.

In another embodiment, the biodegradable carrier for the treatment agent is a polymerosome. A "Polymerosome" is a polymer vesicle formed from di-block or tri-block copolymers with blocks of differing solubility. Polymerosomes may be formed by methods such as film rehydration, electroformation and double emulsion. In some methods, a similar manufacturing technique can be used as that of a liposome to form polymerosomes. For example, a polymerosome can be a di-block copolymer including a block which is hydrophobic, e.g., poly lactic acid, polycaprolactone, n-butyl acrylate, and another block which is hydrophilic, e.g., poly (ethylene glycol), poly(acrylic acid). A polymerosome can be in a range from between about 25 nm to about 2000 nm.

In another embodiment, the biodegradable carrier for the treatment agent is a micelle. A "micelle" is an aggregate of surfactant or polymer molecules dispersed in a liquid colloid. Micelles are often globular in shape, but other shapes are possible, including ellipsoids, cylinders, bilayers, and vesicles. The shape of a micelle is controlled largely by the molecular geometry of its surfactant or polymer molecules, but micelle shape also depends on conditions such as temperature or pH, and the type and concentration of any added salt.

Micelles can be formed from individual block copolymer molecules, each of which contains a hydrophobic block and a hydrophilic block. The amphiphilic nature of the block copolymers enables them to self-assemble to form nanosized aggregates of various morphologies in aqueous solution such that the hydrophobic blocks form the core of the micelle, which is surrounded by the hydrophilic blocks, which form the outer shell. The inner core of the micelle creates a hydrophobic microenvironment for a non-polar treatment agent, while the hydrophilic shell provides a stabilizing interface between the micelle core and an aqueous medium. Examples of polymers which can be used to form micelles include, but are not limited to, polycaprolactone polyethylene oxide blocks, polyethylene oxide-β-polypropylene oxide-β-polyethylene oxide triblock copolymer and copolymers which have a polypeptide or polylactic acid core-forming block and a polyethylene oxide block. A micelle can be in a range from between about 10 nm to about 100 nm.

In another embodiment, the biodegradable carrier for the treatment agent is a nanoparticle (e.g., nanosphere) or microparticle (e.g., microsphere). Various methods can be employed to formulate and infuse or load the particles with the treatment agent. Representatively, the particles are prepared by a water/oil/water (W/O/W) double emulsion method. In the W1 phase, an aqueous phase containing treatment agent, is dispersed into the oil phase consisting of polymer dissolved in organic solvent (e.g., dichloromethane) using a high-speed homogenizer. Examples of polymers include, but are not limited to, poly(D,L-lactide-co-glycolide) (PLGA), poly(D,L-lactide) (PLA) or PLA-PEG co-polymers, poly-ester-amide co-polymers (PEA) and polyphosphazines. The primary water-in-oil (W/O) emulsion is then dispersed in an aqueous solution containing a polymeric surfactant, e.g., poly(vinyl alcohol) (PVA), and further homogenized to produce a W/O/W emulsion. After stirring for several hours, the particles are collected by filtration. A microparticle can be in a range from about 5 μm to about 200 μm, preferably 10 μm to 50 μm. A nanoparticle can be in a range from between about 10 nm to about 500 nm, preferably about 50 nm to about 300 nm.

In some embodiments, the carrier controls a release rate of the treatment agent. The carrier may allow for a slow or sustained release of the treatment agent. Representative sustained-release carriers include encapsulation polymers such as poly (L-lactide), poly (D,L-lactide), poly (glycolide), poly (lactide-co-glycolide), polycaprolactone, polyanhydride, polydioxanone, polyorthoester, polyamino acids, or poly (trimethylene carbonate), and combinations thereof. In this aspect, the polymer forming the carrier controls a release rate of the treatment agent. In some embodiments, the carrier allows for immediate-release or periodic-release of the treatment agent. For example, the carrier allows for periodic-release of a treatment agent such that the treatment agent is released for a short time at relatively regular intervals.

In still further embodiments, a coating may be applied to the treatment agent or the carrier to control a release rate of the treatment agent. In some embodiments, the coating may be a bio-degradable coating such as a gel which decreases a dissolution rate of the treatment agent or carrier within the body. For example, the treatment agent encapsulated within, for example, a microparticle or a nanoparticle, may be dipped into a dilute gelatin solution to provide a gel coating around the microparticle or nanoparticle encapsulated treatment agent. It is further contemplated that both the treatment agent carrier and a coating applied to the carrier modify a release rate of the encapsulated treatment agent.

In some embodiments, the release rate of the treatment agent is tailored to accommodate the ailment to be treated. For example, a carrier encapsulating an antibiotic used to treat an infection can have an intermediate release rate so that the treatment agent is released for a period just long enough to treat an infection whereas a carrier encapsulating a nitric oxide generating treatment agent used to compensate for endothelial dysfunction can have a sustained-release rate so that the treatment agent is released as long as possible. Alternatively, a carrier encapsulating a treatment agent for preventing vulnerable plaques can have a periodic release rate which releases the treatment agent for a short time at regular intervals. Vulnerable plaques result when macrophage activity is heightened to the point that the inside of the plaque is broken down more rapidly than recruited migrating smooth muscle cells can lay down a reinforcing fibrotic matrix. Temporary depression of macrophage activity may allow sufficient recruitment of smooth muscle cells and the laying down of matrix to prevent or delay a vulnerable plaque fibrous cap from becoming too thin and rupturing for long enough to allow the plaque to revert back to a stable plaque when the, as yet unknown, cause of the heightened macrophage activity is gone. It is likely that a slight modification of the balance between the smooth muscle cells laying down matrix and the macrophages breaking down the matrix by a bio-active substance, may prevent a vulnerable plaque rupture.

Since the treatment agent is delivered to peri-adventitial space 210 or the pericardium, the particle size is not limited to the intraluminal dimensions of the blood vessels. In this aspect, the particles may have an average diameter less than 1000 μm. In other embodiments, the average diameter of the particle may be less than 5 μm. Still further, the average diameter of the particle may be between 15 μm and 1000 μm.

The treatment agents may further be delivered in a gel. Representative gels may be one or more component gels including but not limited to, alginate gels, PEG-gels and other suitable hydrogels. Such gels may be suitable for delivery of a treatment agent alone and/or within the above-described carriers. The living biologics may further be co-delivered within a matrix gel or drug loaded particles.

Hydraulic dissection and delivery of the above described treatment agents and solutions may be accomplished by any of the methods and devices which will now be described with reference to FIGS. 5-12. FIGS. 5-12 illustrate various embodiments of a delivery device capable of dissecting tissue planes and delivering treatment agents. In general, the delivery devices provide a system for delivering a substance, such as a treatment agent or a combination of treatment agents adjacent a desired area of a blood vessel to treat a localized area of the blood vessel or to treat a localized area of tissue possibly located adjacent to the blood vessel.

Figure 5:
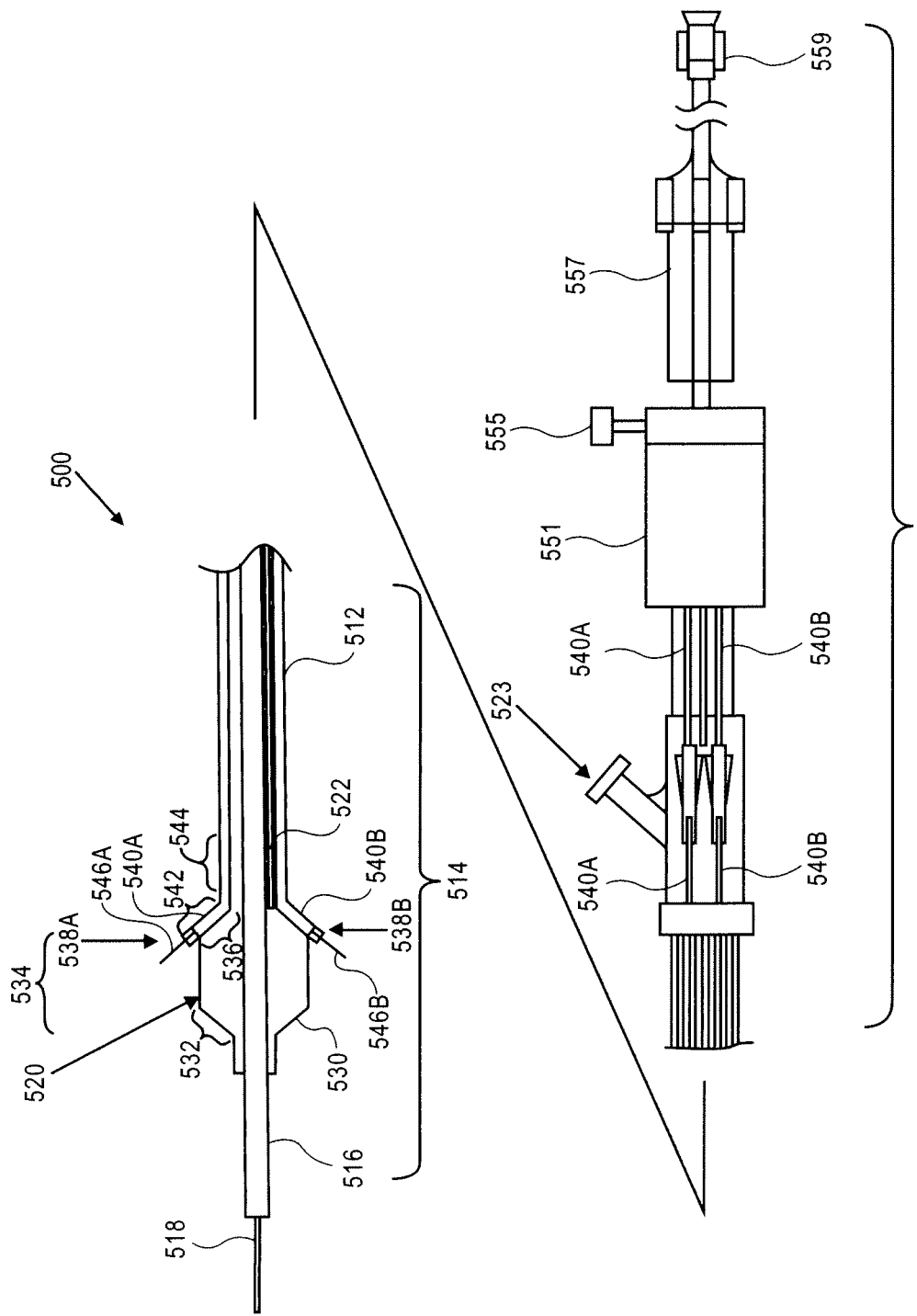
FIG. 5 is a simplified cross-sectional view of an embodiment of a delivery device.

FIG. 5, illustrates a simplified cross-sectional view of an embodiment of an intraluminal delivery device. The delivery device is similar in certain respects to the delivery apparatus described in commonly-owned, U.S. Pat. No. 6,692,466 issued Feb. 17, 2004, titled "Directional Needle Injection Drug Delivery Device", of Chow, et al. The delivery apparatus is further similar in certain respects to the delivery apparatus described in commonly-owned, U.S. Pat. No. 6,702,744 issued Mar. 9, 2004 titled "Agents That Stimulate Therapeutic Angiogenesis and Techniques and Devices That Enable These Devices", of Evgenia Mandrusov et al. and U.S. patent application Ser. No. 10/792,960 filed as a continuation in part of U.S. Pat. No. 6,702,744 on Mar. 3, 2004 titled "Agents That Stimulate Therapeutic Angiogenesis and/or Angiomyogenesis and Techniques and Devices That Enable Delivery", of Evgenia Mandrusov and U.S. patent application Ser. No. 10/781,984 filed as a divisional of U.S. Pat. No. 6,702,744 on Feb. 18, 2004 titled "Agents That Stimulate Therapeutic Angiogenesis and Techniques and Devices That Enable These Devices", of Evgenia Mandrusov et al. The delivery apparatus includes a catheter assembly 500, which is intended to broadly include any medical device designed for insertion into a blood vessel or physiological lumen to permit injection and/or withdrawal of fluids, to maintain the potency of the lumen, or for any other purpose.

In one embodiment, catheter assembly 500 is defined by elongated catheter body (cannula) 512 having proximal end 513 and distal end 514. In one embodiment, catheter assembly 500 includes catheter body 512 extending from proximal end 513 to distal end 514. In this example, guidewire cannula 516 is formed within catheter body 512 for allowing catheter assembly 500 to be fed and maneuvered over guidewire 518 (shown at this point within guidewire cannula 516).

Balloon 520 attaches at distal end 514 of catheter assembly 500 and is in fluid communication with inflation lumen 522 formed within catheter body 512. Balloon 520 includes balloon wall or membrane 530, which is selectively inflatable to expand from a collapsed configuration to a desired and controlled expanded configuration. Balloon 520 can be selectively expanded by supplying a fluid into inflation cannula 522 at a predetermined rate of pressure through inflation port 523. Balloon wall 530 is selectively deflatable, after inflation, to return to the collapsed configuration or a deflated profile. In one embodiment, balloon wall 530 can be defined by three sections, distal taper wall 532, medial working length 534, and proximal taper wall 536. In one embodiment, proximal taper wall 536 can taper at any suitable angle θ, typically between about 10° to less than about 90°, when balloon 520 is in the expanded configuration.

Distal taper wall 532, medial working length 534, and proximal taper wall 536 may be bound together by seams or be made out of a single, seamless material. Balloon 520 may be made from any suitable material, including polymers and copolymers of polyolefins, polyamides, polyesters and the like. The specific material employed must be mutually compatible with the fluids employed in conjunction with balloon 520 and must be able to stand the pressures that are developed within balloon 520. Balloon wall 530 may have any suitable thickness so long as the thickness does not compromise properties that are critical for achieving optimum performance. Such properties include high burst strength, low compliance, good flexibility, high resistance to fatigue, the ability to fold, the ability to cross and re-cross a desired region of treatment or an occluded region in a lumen, and low susceptibility to defect caused by handling. By way of example, and not limitation, the thickness may be in the range of about 10 microns to about 30 microns, the diameter of balloon 520 in the expanded configuration may be in the range of about 2 mm to about 10 mm, and the length may be in the range of about 3 mm to about 40 mm, the specific specifications depending on the procedure for which balloon 520 is to be used and the anatomy and size of the target lumen in which balloon 520 is to be inserted.

Balloon 520 may be inflated by the introduction of the liquid into inflation lumen 522. Liquids containing treatment or diagnostic agents may also be used to inflate balloon 520. In one embodiment, balloon 520 may be made of a material that is permeable to such therapeutic and/or diagnostic liquids. To inflate balloon 520, the fluid may be supplied into inflation lumen 522 at a predetermined pressure, for example, between about one and 20 atmospheres.

Catheter assembly 500 also includes substance delivery assembly 538A for injecting a treatment agent into a tissue of a physiological passageway. In one embodiment, delivery assembly 538A includes needle 546A having a lumen with a diameter of, for example, 0.004 inches (0.010 cm) to 0.012 inches (0.030 cm). Needle 546A is movably disposed within delivery lumen 540A formed in catheter body 512. Delivery assembly 538B includes needle 546B movably disposed within delivery lumen 540B. Delivery lumen 540A and delivery lumen 540B each extend between distal end 514 and proximal end 513. Delivery lumen 540A and delivery lumen 540B may be made from any suitable material, such as polymers and copolymers of polyamides, polyolefins, polyurethanes, and the like. Access to the proximal end of delivery lumen 540A or delivery lumen 540B for insertion of needle 546A or 546B, respectively is provided through hub 551.

One or both of delivery lumen 540A and delivery lumen 540B may be used to deliver a treatment agent to a treatment site (e.g., through needle 546A and/or needle 546B). Alternatively, one delivery lumen (e.g., delivery lumen 540A via needle 546A) may be used to deliver a treatment agent (e.g., anti-inflammatory treatment agent) while the other delivery lumen (e.g., delivery lumen 540B via needle 546B) may be used to deliver a therapeutic substance other than an anti-inflammatory substance.

In one embodiment, delivery lumen 540A and delivery lumen 540B conform to the outer dimensions of cannula body 512 and balloon 520. In this aspect, delivery lumen 540A and delivery lumen 540B include bend regions at which distal sections of delivery lumen 540A and delivery lumen 540B are capable of bending (or generally rotating) about pivotal point with respect to a proximal section. Thus, for example, in response to the inflation of balloon 520, distal section 542 of delivery lumen 540A moves relative to proximal section 544 to form the bend region. In one embodiment, section 542 may move from a substantially longitudinal position to a substantially perpendicular position. Thus, the angle θ of the bend region may vary between 0° and 90°. In one example, after inflation of balloon 520, angle θ may range from between about 10° and 90°, for example, 45°.

Needles 546A and 546B may be slidably or movably disposed in delivery lumen 540A and 540B respectively. Each of needles 546A and 546B may include a tissue-piercing tip having a dispensing port. The dispensing port is in fluid communication with a lumen (not shown) of the needle. In one embodiment, the lumen of, for example, needle 546A may be pre-filled with a measured amount of a treatment agent. The lumen of needle 546A connects the dispensing port with treatment agent injection port 559, which is configured to be coupled to various substance-dispensing means of the sort well known in the art, for example, a syringe or fluid pump. Injection port 559 allows for dispensing a measured treatment agent from the dispensing port as desired or on command.

Needle 546A is coupled at proximal end 513 of catheter assembly 500 in a needle lock 555. Needle lock 555 can be used to secure needle 546A in position once needle 546A has been either retracted or extended from delivery lumen 540A. In one embodiment, an adjustment knob 557 sets the puncture distance of needle 546A as it extends from delivery lumen 540A and into the wall of the physiological lumen. For example, adjustment knob 557 may have calibrations such that each revolution from one calibrated mark to another represents a fixed distance of travel for needle 546A. The portion of needle 546A protruding from delivery lumen 540 can be of any predetermined length; the specific length depending on the desired penetration depth and the procedure for which delivery assembly 538A is to be used. In one embodiment, the protruding length of needle 546A is that which is sufficient to advance the dispensing port through the vessel wall and into the peri-adventitial space. In one aspect, the protruding length of needle 546A may be approximately nine millimeters (mm) or less. It is appreciated that other mechanisms for securing needle 546A at a retracted or extended position may alternatively be used, including the incorporation of a mechanical stop optionally including a signaling (e.g., electrical signaling) device as described in commonly-owned U.S. Pat. No. 6,692,466 issued Feb. 17, 2004, titled "Directional Needle Injection Drug Delivery Device."

Needle 546A is slidably disposed in delivery lumen 540A, so that it can move between retracted and extended positions. In its retracted position, the tissue-piercing tip lies inboard of the distal surface of catheter body 512, so as to avoid damaging tissue during deployment of catheter assembly 500. In its extended position, the tissue-piercing tip lies outboard of the distal surface of catheter body 512, so as to permit the needle tip to penetrate the tissue surrounding the physiological passageway and extend into, for example, the peri-adventitial or pericardial space.

Figure 6:
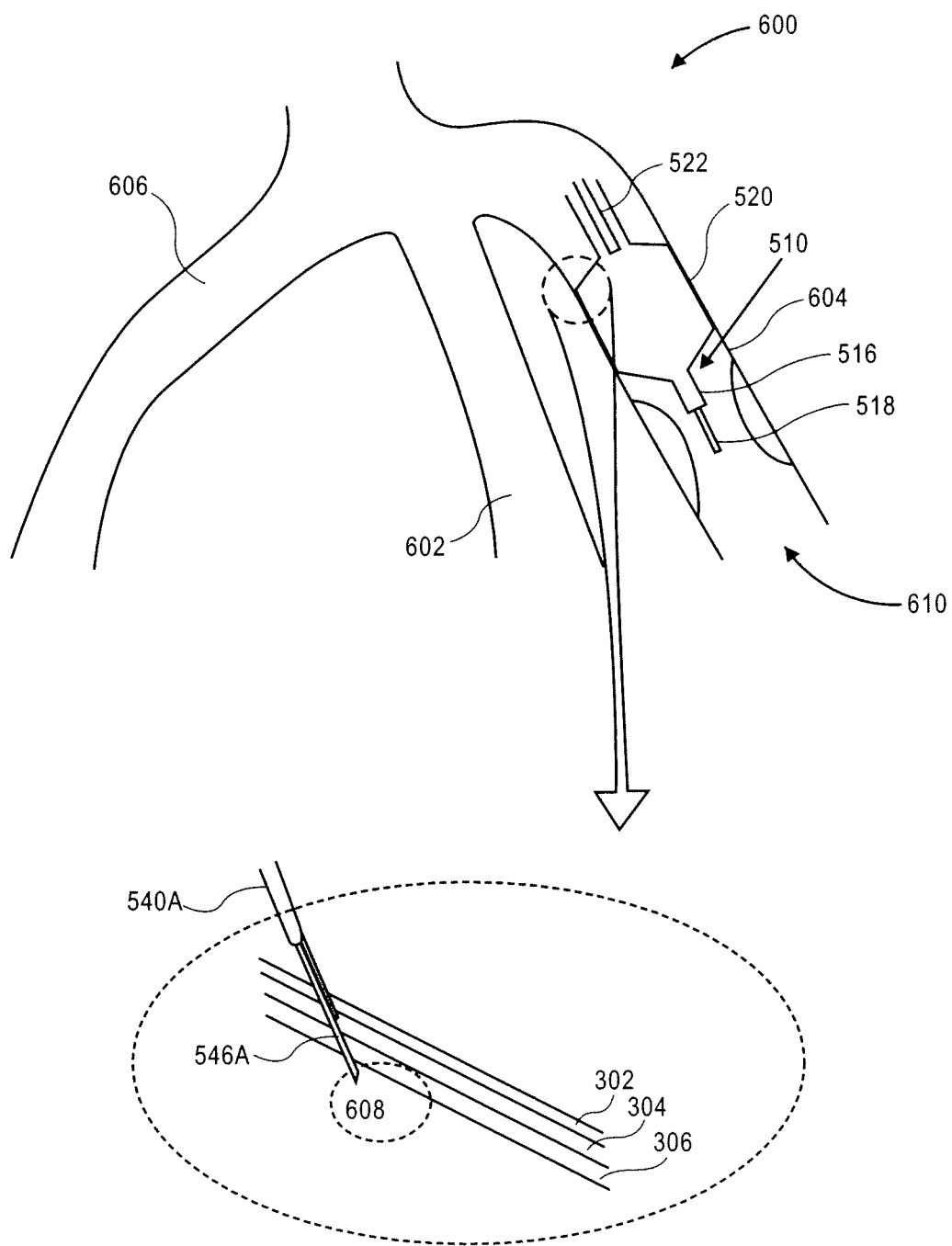
FIG. 6 schematically illustrates a left coronary artery network having a catheter assembly introduced therein.

FIG. 6 illustrates the introduction of catheter assembly 500 into a left coronary artery network. In this simplified example, vasculature 600 includes left anterior descending artery (LAD) 602, left circumflex artery (LCX) 604 and right coronary artery (RCA) 606. Site 608 represents a region within the peri-adventitial space. Occlusion 610 is shown in LCX 604. Occlusion 610 limits the amount of oxygenated blood flow through LCX 604. Accordingly, the treatment site within the peri-adventitial space is shown adjacent the occluded region.

To improve the function of the artery network, it is generally desired to remove occlusion 610 (for example through an angioplasty procedure), bypass occlusion 610, or induce therapeutic angiogenesis to makeup for the constriction and provide blood flow to the ischemic region (e.g., the region downstream of occlusion 610). Additionally, a treatment agent may be introduced to the diseased region. In the illustrated embodiment, guidewire 518 is introduced into the arterial system 600 of the patient (e.g., through the femoral artery) until the distal end of guidewire 518 is upstream of a narrowed lumen of the blood vessel (e.g., upstream of occlusion 610). Alternatively, guidewire 518 may be introduced into the venous system of the patient. Catheter assembly 500 connects to the proximal end of guidewire 518 and advances over the guidewire 518 until catheter assembly 500 is positioned as desired. FIG. 6 shows the catheter assembly 510 positioned so that balloon 520 and delivery lumen 540A are upstream of the narrowed lumen of LCX 604. Angiographic, fluoroscopic or other guidance techniques as previously discussed may be used to position catheter assembly 500. Once balloon 520 is placed and subject to low inflation pressure, guidewire 518 is removed and replaced in one embodiment with an optical fiber (not shown). For example, an imaging portion of an imaging device (e.g., OCT, ultrasonic, etc.) may be within an imaging lumen as the catheter is positioned. Once positioned, in this case upstream of occlusion 610, the imaging assembly may be used to view the blood vessel and identify its various layers. The imaging assembly may provide viewable information about the thickness of the various layers of the blood vessel wall of LCX 604. In this aspect, a treatment site within a peri-adventitial space 608 adjacent to LCX 604 may be identified.

In one embodiment, for example, delivering a liquid or gas to balloon 520 through inflation lumen 522 expands the balloon 520. The inflation of balloon 520 causes delivery lumen 540A to move proximate to or contact the blood vessel wall adjacent to the treatment site. Needle 546A is then advanced a distance. The thickness of the blood vessel wall and the proximity of the exit of delivery lumen 540A to the blood vessel wall determine this distance. Once the needle advances this distance, its dispensing port lies within peri-adventitial space 608. A real time image may be used to advance needle 546A. Alternatively, the advancement may be based on a measurement of the blood vessel wall or layer boundary derived from an optical image. Adjustment knob 557 (See FIG. 5) may be used to accurately locate needle tip 546A in the desired peri-adventitial region 608. Once in position, a treatment agent may be introduced through needle 546A to the treatment site (e.g., peri-adventitial site 608 or a pericardial space).

A volume of the treatment agent or solution within injection port 559 is dispensed from the dispensing port at a pressure sufficient to hydraulically dissect tissue planes within the space. In some embodiments, a saline solution hydraulically dissects the tissue planes. In this aspect, once the solution dissects the tissues, a negative pressure may then drain the saline from the space through catheter assembly 500. Once drained, a volume of the treatment agent may be loaded within injection port 559 and delivered from the dispensing port and into the hydraulically dissected tissue.

Dissecting the tissue planes allows a greater volume of treatment agent to be delivered to the treatment site within the peri-adventitial space at one time than not dissecting the tissue planes. In this aspect, a volume of the treatment agent delivered to the peri-adventitial space at one time may be greater than approximately 5 cc. In other embodiments, the volume of fluid delivered may be between approximately 5 cc and 20 cc. Still further, the volume of fluid delivered may be between approximately 10 cc and 20 cc.

Figure 7:
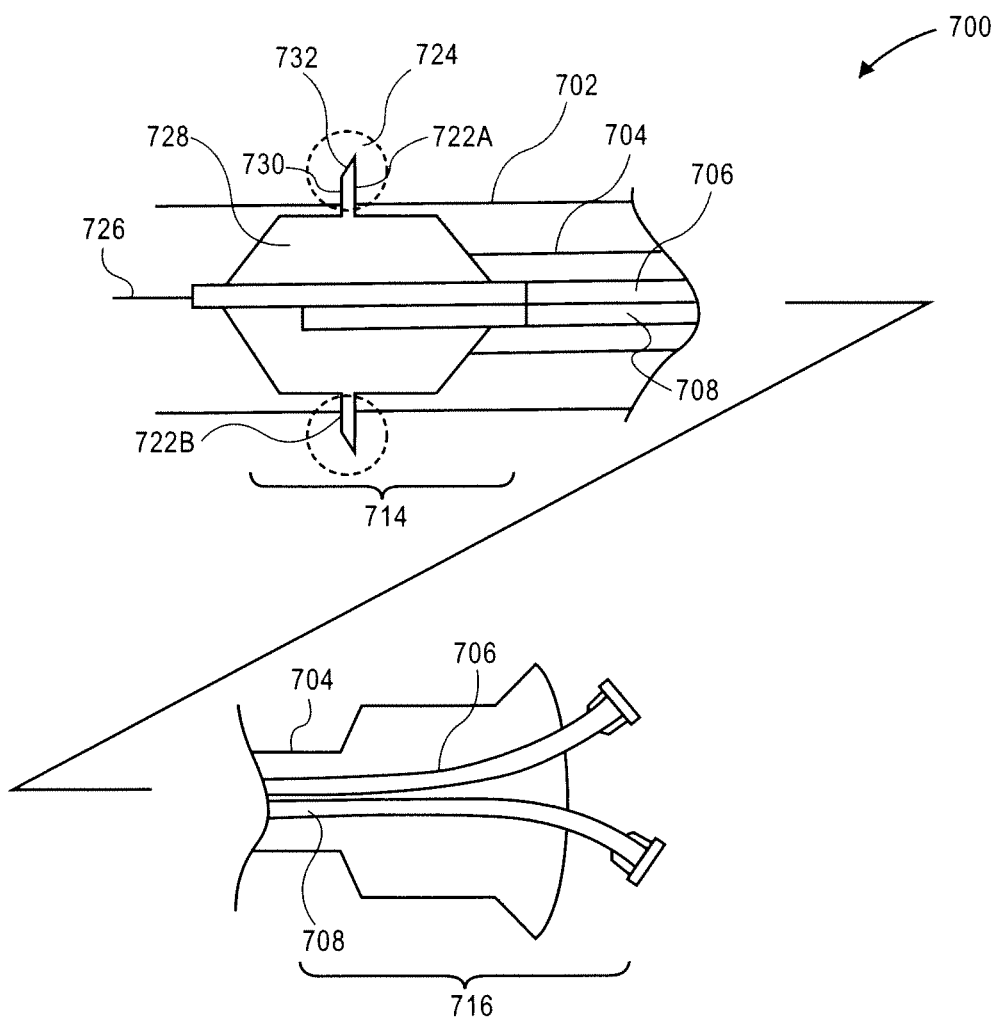
FIG. 7 is a simplified cross-sectional view of another embodiment of a delivery device in the form of a catheter assembly having a balloon and needle assembly.

FIG. 7 is a simplified cross-sectional view of another embodiment of a delivery device in the form of a catheter assembly having a balloon and needle assembly. In particular, in this embodiment, catheter assembly 700 is a "spiked" balloon catheter having a balloon 728 with needles 722A, 722B incorporated into its surface. Needles 722A, 722B may have dimensions substantially similar to those of the needles discussed in regard to FIG. 5. A proximal portion 716 of catheter assembly 700 may be external to a blood vessel 702 and to the patient while a distal portion 714 is within vessel 702. Representatively, catheter assembly 700 may be inserted through a femoral artery and guided through, for example, a guide catheter 704 with a guidewire 726 to a location in the vessel. Alternatively, guidewire 726 may be introduced into the venous system of the patient. FIG. 7 shows distal portion 714 of catheter assembly 700 positioned at a point within vessel 702 adjacent to a treatment site within peri-adventitial space 724.

In one embodiment, catheter assembly 700 includes primary cannula 704 having a length that extends from proximal portion 716 (e.g. located external to a patient during a procedure) to connect with a proximal end or skirt of balloon

728. Primary cannula 704 has a lumen therethrough that includes guidewire cannula 706 and delivery cannula 708. Delivery cannula 708 may extend from proximal portion 714 of catheter assembly 700 to distal portion 716. Delivery cannula 708 has a distal end that terminates within balloon 728. In one embodiment, a fluid or treatment agent may be introduced through delivery cannula 708 to expand balloon 728 within vessel 702.

Similar to the balloon illustrated in FIG. 5, balloon 728 includes a balloon wall or membrane which is selectively inflatable from a collapsed configuration to a desired and controlled expanded configuration. Balloon 728 may be selectively inflated by supplying a fluid into delivery cannula 728 or alternatively an inflation cannula (not shown) at a predetermined rate through an inflation port. The balloon is selectively deflatable to return to the collapsed configuration or a deflated profile. The balloon wall may be made of any suitable material, including polymers, copolymers of polyolefins, polyamides, polyesters and the like. Balloon 728 may have any suitable thickness so long as the thickness does not compromise properties that are critical for optimum performance. By way of example, and not limitation, the thickness may be about 10 microns to about 30 microns, the expanded diameter of balloon 728 may be about 2 mm) to about 10 mm, and the length may be about 3 mm to about 40 mm. The specific specifications depend on the procedure that balloon 728 is to be used in and the anatomy and size of the target lumen in which balloon 728 is to be inserted.

FIG. 7 shows first needle 722A and second needle 722B on a surface of balloon 728. Any number of needles may be located along the surface of balloon 728. The needle may be connected to the surface of balloon 728 by, for example, an adhesive such as cyanoacrylate. Needle 722A may include hollow shaft 730 and tip 732 having an outlet port. Needle 722A connects to delivery cannula 708 to permit delivery of a treatment agent through the outlet port of needle 722A. Needle 722B is substantially the same as needle 722A. In other embodiments, catheter assembly 700 may include a separate inflation lumen and a number of delivery cannulas equal to that of the needles. In this aspect, each needle may connect with a separate delivery cannula so as to allow each needle to deliver different fluids simultaneously while the inflation lumen is used to inflate balloon 728.

In one embodiment, any of the solutions or treatment agent previously discussed may be delivered through delivery cannula 708 to balloon 728. The solution or treatment agent may be used to expand balloon 728 causing needle 722A to move in a substantially perpendicular direction, relative to a longitudinal axis of balloon 728, and pierce the vessel wall into peri-adventitial space 724. Needle 722A may then deliver the solution or treatment agent into peri-adventitial space 724. In some embodiments, needle 722A is advanced through peri-adventitial space 724 and into the pericardial space as previously discussed for delivery of the treatment agent to this region.

In one embodiment, fluid volume, pressure and flow rate are controlled manually via a syringe. In another embodiment, fluid pressure is controlled by a pressurized reservoir, such as a pressurized IV bag. In another embodiment, flow rate may be controlled by an IV pump. In still further embodiments, the delivery device may have a pressure gauge or relief valve to aid in manual control or pressure.

Various techniques are used to prevent needles 722A and 722B from piercing the vessel wall during advancement and withdrawal of catheter assembly 700 through the vessel. In one embodiment, balloon 728 is deflated and needles 722A and 722B are positioned between folds of balloon 728. Folds of balloon 728 may be set in a heat forming process to hold the folds during catheter delivery and to cause the balloon to re-fold in the same manner when the balloon is deflated. Representatively, the deflated balloon cross-section at the needles may look like an "H" and the needles may be positioned between the "I" portions of the "H". Away from the needles the balloon folds may be wrapped to produce distal and proximal bevels to aid in atraumatic catheter movement.

In other embodiments, needles 722A and 722B are positioned along deflated balloon 728 parallel to a longitudinal axis of catheter assembly 700. For example, a partially deflated balloon 728 is positioned within the vessel and then withdrawn slightly to ensure needle disengagement from the vessel wall. A guidewire or wire-like device is then advanced through a cannula in communication with a lumen of needles 722A and 722B. The wire-like device includes a stiff portion that is advanced into the base of needles 722A and 722B causing a polymer cannula with elastomeric properties that would normally direct needles 722A and 722B toward the wall to be straightened. This, in turn, causes needles 722A and 722B to lay down parallel to the longitudinal axis of catheter assembly 700 during the completion of balloon deflation so that the folds of balloon 728 cover needles 722A and 722B. Such a wire-like device includes mechanical interferences with the needle and cannula and dimensions, such that it can only be advanced to position part of the stiff portion in a distal portion of the polymer and the proximal portion of needles 722A and 722B to effect the straightening. Such a wire-like device can also be configured to be completely withdrawn from the catheter to allow injection through needles 722A and 722B or dimensioned such that it need only be withdrawn a short distance (i.e., a major portion of the wire remains inside the catheter) while still leaving enough space in the cannula for an injection to be performed. If the design allows a partial wire-like device withdrawal, a rotating hemostasis valve type device (e.g., a hemostasis valve with side-arm) can be used to facilitate longitudinal motion of the wire-like device, sealing around the wire-like device and injection (via the side-arm).

In still further embodiments, a sheath or portion of a sheath is advanced over balloon 728 causing needles 722A and 722B to lie down along a surface of balloon 728 during insertion and withdrawal of catheter assembly 700 within the vessel. The sheath is removed once catheter assembly 700 is positioned at the desired location within the vessel to allow for delivery of a treatment agent as previously described.

Catheter assembly 700 may be an over the wire (OTW) configuration wherein guidewire cannula 706 extends from a proximal end (external to a patient during a procedure) to a distal end of catheter assembly 700. Guidewire cannula 710 may also be used for systemic delivery of a treatment agent. In another embodiment, catheter assembly 700 is a rapid-exchange-type (RX-type) catheter assembly, and only a portion of catheter assembly 700 (a distal portion 714 including balloon 728) advances over guidewire 726. In an RX-type catheter assembly, typically, the guidewire cannula and lumen extends from the proximal end of the catheter assembly. The proximal guidewire port is typically spaced a substantial distance from the proximal end of the catheter assembly.

Figure 8A:
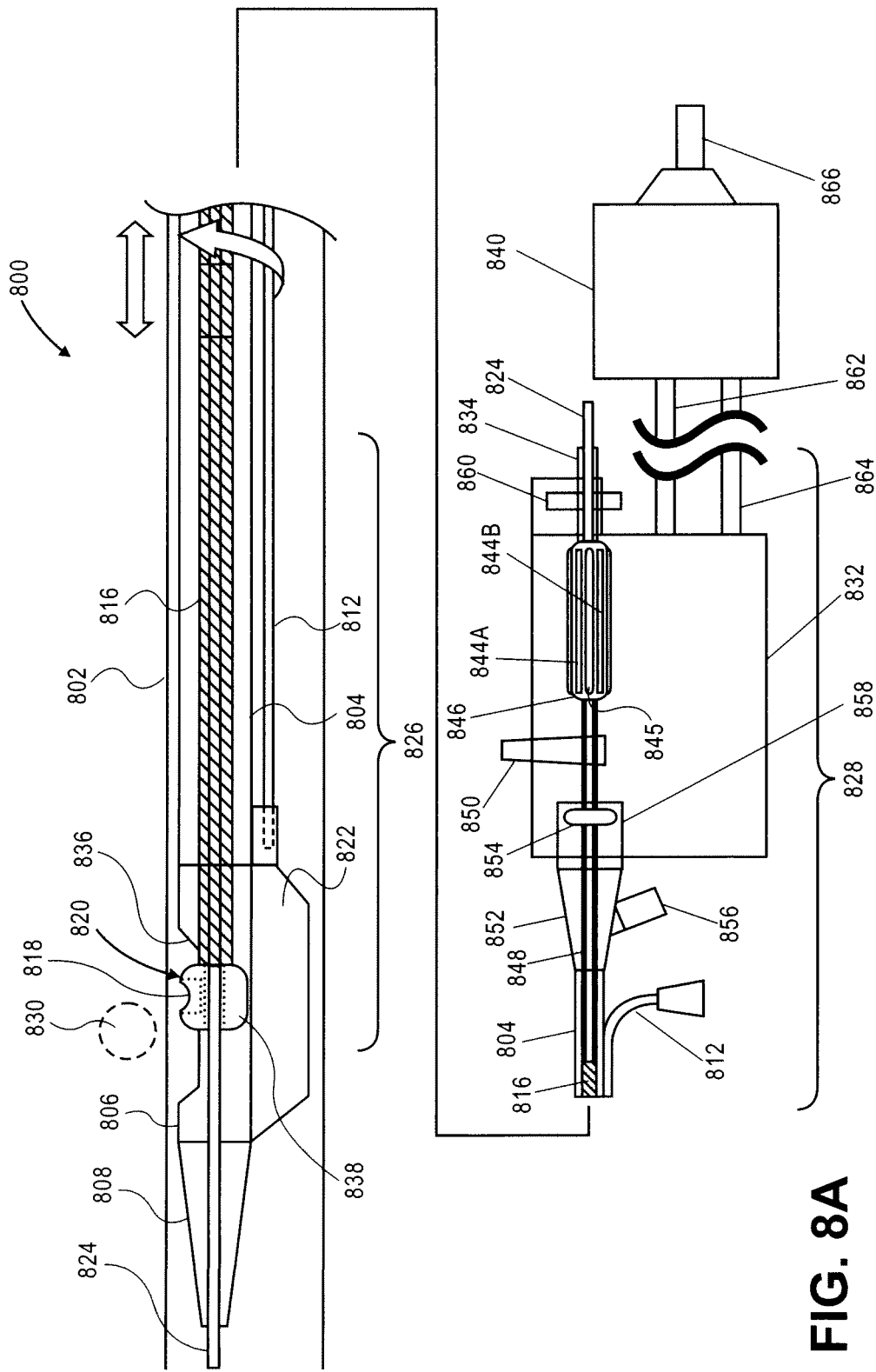
FIG. 8A is a simplified cross-sectional view of another embodiment of a delivery device in the form of a modified atherectomy device.

FIG. 8A is a simplified cross-sectional view of another embodiment of an intraluminal delivery device in the form of a catheter assembly including an imaging assembly for imaging vessel features to locate a desired treatment site. In this embodiment, the imaging assembly is positioned within a modified atherectomy device similar in certain respects to the delivery apparatus described in commonly-owned, U.S. Pat. No. 5,865,748 issued Feb. 2, 1999, titled "Guided Directional Coronary Atherectomy Distal Linear Encoder."

Catheter assembly 800 includes a proximal end 828 and a distal end 826. Proximal end 828 of catheter assembly 800 is external to blood vessel 802 and to the patient while distal end 826 is within vessel 802. Representatively, catheter assembly 800 is inserted through a femoral artery and guided through, for example, primary cannula 804 with guidewire 824 to a location within the vessel. Alternatively, guidewire 824 is introduced into the venous system of the patient. In still further embodiments, a sheath (not shown), may be inserted into the brachial or femoral artery and advanced in a well known manner through the vasculature toward the heart. Alternatively, the sheath may be introduced into the venous system. Catheter assembly 800 may then be inserted into a proximal end of the sheath and guided through the arteries by fluoroscopy to a position in blood vessel 802 adjacent a treatment site within peri-adventitial space 830. FIG. 8A shows distal end 826 of catheter assembly 800 positioned at a point within vessel 802 adjacent to a treatment site within peri-adventitial space 830.

Cable 816 includes a duplex spring to facilitate rotation of imaging assembly 820. A duplex spring is a spring inside a spring and usually multi-filar (more than one wire used to construct each spring), a very miniature coaxial cable or other electrical cable(s) having a polymer sheath or impregnating polymer on its outer diameter. The outer winding (spring) of the duplex spring is open wound (there is a gap between the filars/wires of the outer spring) and the coaxial cable or other electrical cable(s) is placed/wound into this gap and held in place by the sheath/impregnation. In some embodiments, cable 816 is a single insulated conductor and the stainless steel duplex spring acts as the other conductor. At their distal ends the two conductors are electrically connected to transducer 818 and at their proximal ends to electrical connections (brushes or slip ring-like surfaces) 844a 844b of electro-mechanical connector 846. Electro-mechanical connector 846 is attached to the proximal end of a stiffened section 848 of cable 816.

The proximal end of cable 816 has a stiffened section 848 that allows cable 816 to be manually advanced or retracted by thumb lever 850. In some embodiments, stiffened section 848 is a stainless steel hypotube-like component attached to the duplex spring or outer diameter of the sheath on cable 816. Thumb lever 850 mechanically engages (engagement features not shown) stiffened section 848 such that stiffened section 848 may rotate, but not translate longitudinally relative to thumb lever 850. Stiffened section 848, is positioned such that it completely fills proximal hub 852 (i.e., there is no flexible cable 816 section in the hub 852) with thumb lever 850 in its most proximal position to prevent cable 816 buckling in hub 852. Thumb lever 850 may be rotated slightly to engage (or disengage) the housing of the catheter interface unit 832 with a frictional/interference to lock (unlock) the position of the thumb lever 850 when desired.

Proximal hub 852 is an RHV-like (Rotating Hemostasis Valve) device attached to primary cannula 804. It contains a seal or seal assembly 854 that forms a seal around an outer diameter of stiffened section 848 such that when fluid is injected into flush port 856, flow is directed into annular space between the outer diameter of cable 816 and an inner diameter of primary cannula 804 and not out of the proximal end of hub 852. The proximal end of the hub 852 is configured to be an interference fit connection 858 that retains hub 852 in catheter interface unit 832. Proximal hub 852 also includes a seal and features (not shown) that allow interference fit connection 858 to rotate relative to the rest of proximal hub 852.

Catheter interface unit 832 (a hand held unit) and electro-mechanical connector 846 having raised portions 845 engage such that catheter interface unit 832 applies rotation to the connector 846 in a manner that allows cable 816 to be moved longitudinally proximal or distal by moving thumb lever 850. Additionally, it contains electrical connections (electrical brushes and slip rings and/or slip ring-like surfaces) that provide electrical connection access to transducer 818. On the proximal end of connector 846 are thumb wheel 860 and port 834. Port 834 enables access to the open inner diameter/lumen that runs continuously through thumb wheel 860, connector 846, cable 816 and support mechanism 838. Guidewire 824 is shown occupying that lumen. In another embodiment, the device 800 is a fixed guidewire device, such that a guidewire-like tip is attached to the distal end of nosecone 808 and thus, needle 842 may reside in the lumen (in a retracted position) during catheter positioning/imaging or inserted at another time in the procedure prior to injection. In some embodiments, port 834 and/or the housing of catheter interface unit 832 may be configured to releasably attach to a needle advancement control device (not shown). Thumbwheel 860 allows the operator to manually rotate the cable 816 to rotationally orient the support mechanism 838/imaging assembly 820 in the desired direction for needle 842 advancement. The thumbwheel 860 and/or the catheter interface unit 832 may contain elements (not shown) to only allow thumbwheel 860 (and thus cable 816 and other components) rotation in the preferred direction.

In one embodiment, catheter assembly includes primary cannula 804 having a length that extends from proximal end 828 (e.g. located external to the patient) to connect with a proximal end of balloon 822. Delivery cannula 812 extends from distal end 826 of catheter assembly 800 to proximal end 828. A distal end of delivery cannula 812 terminates within balloon 822. Delivery cannula 812 is a part of or attached to primary cannula 804 (e.g., by capturing both cannulas inside a heat shrinkable tube (not shown)). In some embodiments, delivery cannula 812 is attached to an outer diameter of primary cannula 804. Delivery cannula 812 can be spiraled around primary cannula 804 outer diameter.

In one embodiment, a fluid (usually a fluoroscopic contrast agent solution) is introduced through delivery cannula 812 to expand balloon 822 within vessel 802.

Catheter assembly 800 further includes imaging assembly 820 so that an image of vessel 802 can be viewed to identify a desired treatment region. Since the wall of vessel 802 and the adjacent anatomy can be viewed by a user prior to injection, injection into adjacent vessels, the pericardial sac and/or muscle tissue can be avoided. In addition, it is recognized that vessel wall thickness varies with vessel size and disease state. Therefore imaging assembly 820 is further used to facilitate measuring of the vessel wall thickness and in turn a depth a needle must penetrate the vessel wall to enter peri-adventitial space 830. In this aspect, catheter assembly 800 provides a stable platform from which to advance a needle through the wall of vessel 802 and have it reliably penetrate into peri-adventitial space 830.

Cable 816 is connected to imaging assembly 820 at one end and catheter interface unit 832 at another end to facilitate rotation of imaging assembly 820. Cable 816 includes a lumen therethrough to accommodate guidewire 824 inserted through port 834. Guidewire 824 can be advanced through catheter assembly 800 by inserting guidewire 824 through port 834 and advancing it through the lumen of cable 816 and imaging assembly 820.

Imaging assembly 820 includes a transducer 818 attached to a support mechanism 838. Support mechanism 838 is attached to an end of cable 816 and has an opening therethrough to accommodate guidewire 824. Support mechanism 838 can be any size and shape capable of being rotated and translated within housing 806 and can be of any material suitable for supporting transducer 818. Transducer 818 generates a series of ultrasonic pulses which are transmitted outward from transducer 818. Echo pulses reflected from the wall of blood vessel 802 are received by transducer 818 between transmitted pulses of transducer 818 and collected by a control imaging system (not shown) connected to catheter 800 via the catheter interface unit 832, electrical cable 862 proximal patient interface unit 840 and electrical cable 866 to be displayed as a cross-sectional ultrasonic image of blood vessel 802.

To facilitate imaging, imaging assembly 820 is positioned within housing 806 having window 836 formed therein. In one embodiment, housing 806 is a cylindrically shaped body attached at one end to nose cone 808 and primary cannula 804 at another end. In one embodiment, nosecone 808 and the distal end of primary cannula 804 will contain features (not shown) that limit the longitudinal motion (proximal and distal) of the imaging assembly 820. Nose cone 808 is a substantially cone shaped structure having openings at both ends to allow guidewire 824 to pass through it. Nose cone 808 provides a flexible tapered tip to catheter assembly 800 to facilitate advancement of catheter assembly 800 through vessel 802. In addition, in some embodiments, support mechanism 838 includes a cutting edge on its distal outer diameter for removing an atheroma of vessel 802 when imaging assembly 820 is rotated and advanced distally. In this aspect, nose cone 808 provides a storage space for the cut atheroma tissue. Housing 806 may be made of any material suitable to support the inflated balloon 822 in the vessel without deformations that impede the motion of the imaging assembly 820. Representative materials include a polymer such as polyetheretherketone (PEEK) or a metal such as stainless steel. Window 836 is formed in the surface of housing 806 at an approximately 120 degree angle or smaller (but large enough to accommodate the needle outer diameter) with respect to the housing's center axis. Imaging assembly 820 is rotated as illustrated by arrows in FIG. 8A within housing 806 to achieve a section image of the wall of blood vessel 802 and the adjacent anatomy through window 836. To achieve additional views, primary cannula 804 may be rotated by an attending physician to rotate window 836 to obtain a views of other portions of blood vessel 802 and the adjacent anatomy. Housing 806 may include encoder structures (not shown) adjacent window 836 for indicating movement of transducer 818 along a linear axis of housing 806 through window 836. During operation, the encoder structures return one of the echo pulses in response to transducer transmitted pulses to indicate angles of revolution thus defining linear movement of transducer 818 through the area of window 836. This information is than transmitted to the control imaging apparatus via cable 816 for analysis. In another embodiment, the longitudinal position of the transducer 818 and associated components may be detected in the catheter interface unit 832, preferably by detecting the position of thumb lever 850 using conventional methods/components (not shown).

A patient interface unit 840 is connected to catheter interface unit 832 to facilitate the transmission of ultrasonic pulses, echo signals and the rotation and translation of imaging assembly 820. In this aspect, patient interface unit 840 includes a motor or other type of apparatus for rotating imaging assembly 820 via cable 816 and circuitry which generates or transmits pulses at predetermined degrees of rotation of proximal end of cable 816 or of the motor (not shown) for enabling transducer 818 to generate an ultrasonic pulse. In some embodiments, imaging assembly 820 is mechanically rotated by cable 816 due to the mechanical rotation provided by the motor (not shown) located in the patient interface unit 840 and provided to the catheter interface unit 832 via a torque cable assembly 864. In one embodiment, the functions of the catheter interface unit 832 and the patient interface unit 840 are combined into a single unit.

A balloon 822 is mounted on a bottom of housing 806 to hold catheter assembly 800 in place once a desired vessel region is identified and the balloon 822 is inflated. Balloon 822 is substantially the same as the balloons previously described herein however is mounted to only a portion of housing 806 such that it does not cover window 836. Balloon 822 is deflated to facilitate rotation and/or translation of catheter assembly 800 within the vessel 802. Balloon 822 is inflated by delivering a fluid through delivery cannula 812 to balloon 822. Inflation of balloon 822 presses window 836 of housing 806 against the desired vessel region.

Figure 8B:
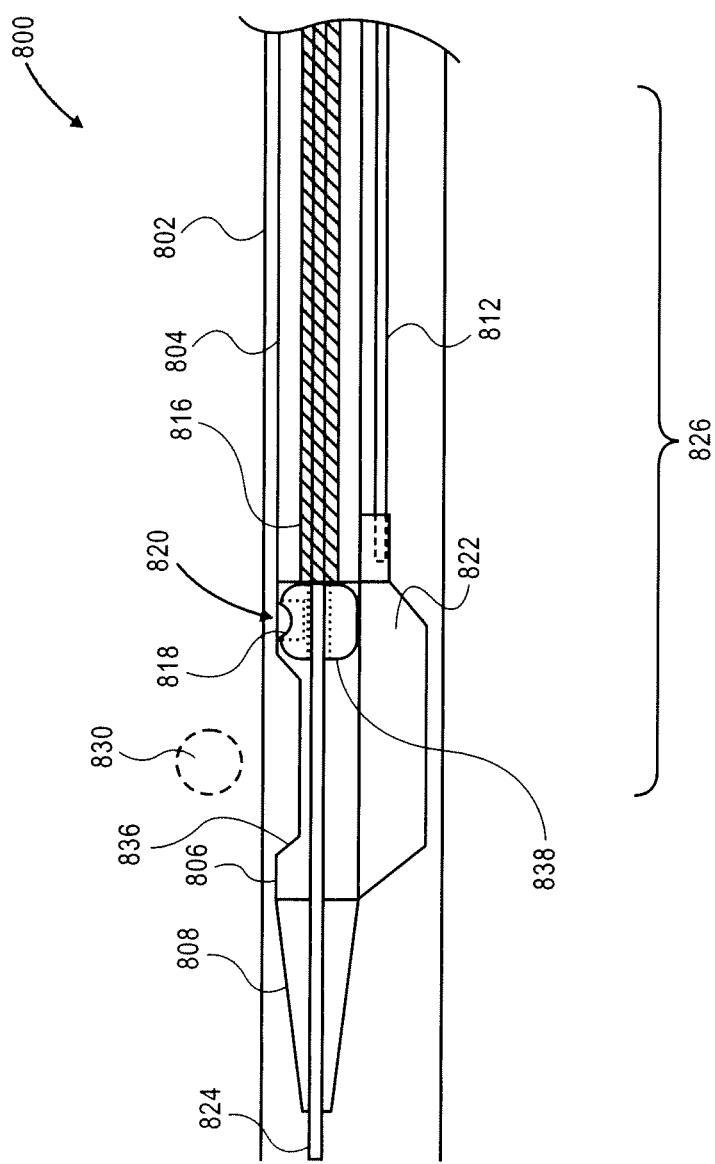
FIG. 8B is a simplified cross-sectional view of the device of FIG. 8A.

FIG. 8B shows the distal end of catheter assembly 800 with guidewire 824 removed. When a desired vessel region is identified, a fluid is delivered to balloon 822 via delivery cannula 812 to inflate balloon 822 and hold catheter assembly 800 in place. Guidewire 824 is then removed as shown to allow for insertion of a needle through cable 816. Imaging assembly 820 is further withdrawn proximally from window 836 to a proximal end of housing 806 prior to needle 842 advancement out of imaging assembly 820. In another embodiment, the needle 842 exits proximal of or from a proximal portion of the imaging assembly 820 and imaging assembly 820 is advanced distal of the window 836 to a distal end of housing 806 prior to needle 842 advancement.

Figure 8C:
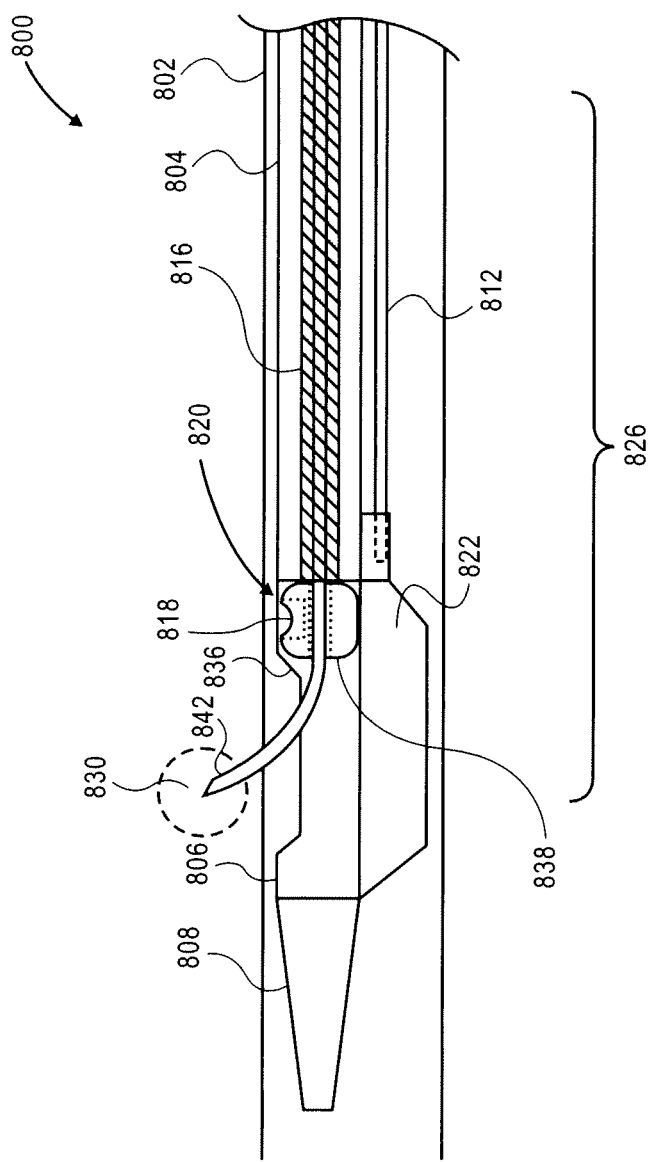
FIG. 8C is a simplified cross-sectional view of the device of FIG. 8A.

FIG. 8C shows the distal end of catheter assembly 800 having a needle 842 inserted as previously described and advanced through window 836 and into a desired vessel region. Needle 842 may be a curved end needle having an outer diameter (OD) near that of a 0.014" OD guidewire. In some embodiments, needle 842 is made out of a shape memory and/or superelastic alloy such as nickel-titanium (NiTi). In this aspect, needle 842 may be substantially straightened during advancement through catheter assembly 800 and then return to its curved shape once it exits the lumen of support mechanism 838. In a fixed guidewire type design, the needle 842 is preferred to be substantially straight and the lumen of support mechanism 838 curved to cause the needle 842 to exit it at an angle to the housing 806 centerline. It is therefore contemplated that housing 806 can include additional features such as a hole(s) or indent(s) that allow transducer 818 to be turned toward that feature by turning thumb wheel 860 and observing the image produced. For example, in some embodiments, a hole is formed in the proximal portion of the housing 806. When imaging assembly 820 is retracted into housing 806 and turned using thumb wheel 860 (prior to needle advancement into the vessel wall), the image seen when the transducer 818 is oriented toward this hole will be very different from the image seen when transducer 818 is orientated toward the wall of housing 806. Thus the orientation of the support mechanism 838 relative to the window 836 may be known/controlled.

In addition, features (e.g. holes or indents) (not shown) between imaging assembly 820 (support mechanism 838) and/or the lumen of cable 816 and needle 842 can be included to orient the distal end of needle 842 relative to imaging assembly 820/support mechanism 838 during its advancement. With proper attention to the design, when the hole, indent or other feature is seen in the image, the curve or exit angle of needle 842 will be aimed toward window 836 (e.g., by a mechanical interference such as by the shapes of the outer diameter of the needle 842 and the inner diameter of the cable or imaging assembly, and/or a tang on an outer surface of needle 842 engaging a slot or groove in the inner diameter of cable 816 or imaging assembly 820 while advancing it or in order to advance it).

During operation of catheter assembly 800, needle 842 is inserted into cable 816 through port 834. Needle 842 is advanced through cable 816 and out an end of support mechanism 838 of imaging assembly 820. Once needle 842 reaches window 836 it curves and extends through window 836 and into the wall of vessel 802. Needle 842 can be advanced or retracted through catheter assembly 800 until it penetrates vessel 802 to a desired depth, e.g. within peri-adventitial space 830. Fluids may then be delivered through needle 842 to peri-adventitial space 830 to hydraulically dissect and deliver a desired treatment agent as previously described.

In the above described intraluminal embodiments for hydraulically dissecting tissues of the peri-adventitial space and locating a treatment agent within the peri-adventitial space, it is appreciated that an opening is made in or through the blood vessel. In some instances, it may be desirable to plug or fill the opening following delivery of the treatment agent. This may be accomplished by introducing through a catheter lumen cyanoacrylate or similar material that will harden on contact with blood.

Figure 9:
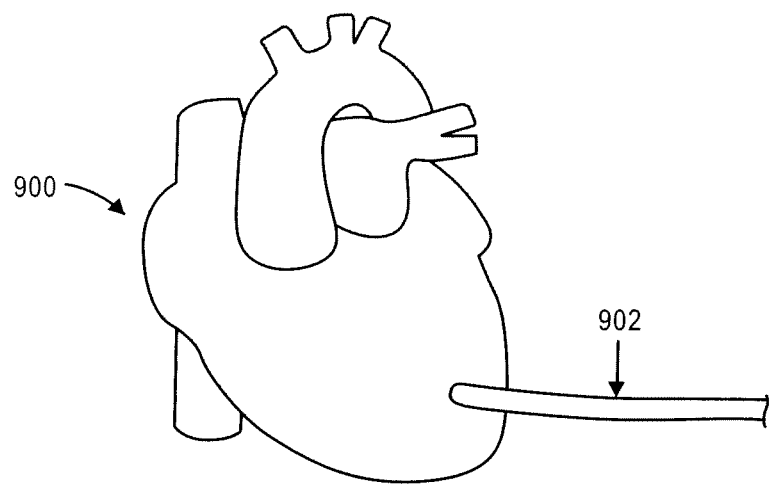
FIG. 9 schematically illustrates an epicardial access system in relation to the heart.

FIG. 9 schematically illustrates an epicardial access system in relation to the heart. In general, the delivery device provides a system for delivering a substance, such as a treatment agent or a combination of treatment agents optionally, from outside of the heart to treat a localized area of the blood vessel or to treat a localized area of tissue located adjacent to the blood vessel. The delivery apparatus of FIG. 9 is similar in certain respects to the delivery apparatus described in commonly-owned, U.S. patent application Ser. No. 11/159,705, filed on Jun. 23, 2005, titled "Method and System for Accessing A Pericardial Space", of Peter L. Callas, et al.

FIG. 9 is a general illustration of an epicardial access device 902 in relation to a heart 900. As shown in greater detail in FIG. 10, device 902 is positioned adjacent a pericardium of heart 900. As previously discussed, a pericardialspace 1002 lies between visceral layer 1004A and epicardium 1004B of the pericardium. Fibrous layer 1000 of the pericardium overlays visceral layer 1004A. Myocardium 1006 is adjacent a side of epicardium 1004B opposite that of pericardial space 1002. A vein or artery 1008 having an overlying fat layer 1005 lies between epicardium 1004B and myocardium 1006. Surrounding vein 1008 beneath fat layer 1005 is peri-adventitial space 1010.

In one embodiment, epicardial access device 902 includes a shaft 1012 and a needle 1014 fixed in relation to a longitudinal axis of shaft 1012 (i.e. needle 1014 is prevented from moving longitudinally with shaft 1012). Shaft 1012 extends from a proximal end (not shown) to a distal end 1016 and is provided with an atraumatic tip 1018. Shaft 1012 is sized so that distal end 1016 can be brought into proximity with pericardium 1000 while the proximal end is accessible from outside of the chest cavity. Shaft 1012 includes a cavity or recessed region 1020 having a depth, d, disposed near distal end 1016, preferably somewhat proximal relative to distal tip 1018 of shaft 1012. A suction lumen 1022 extends from a proximal port (not shown) near the proximal end of the shaft adapted for connecting to a source of negative pressure to a suction port 1024 disposed at recessed region 1020 of shaft 1012. In other embodiments, the cavity or region 1020 includes a plurality of ports distributed at various locations to optimize the suction force applied to the pericardium (i.e., fibrous layer 1000, visceral layer 1004A and epicardium 1004B). In one embodiment, cavity 1020 is defined by a substantially concave cavity wall. In other embodiments, cavity 1020 is other shapes and configurations.

Needle 1014 may be a hollow tubular structure defining an inner bore 1026 and having a sharp distal tip 1028. Needle tip 1028 protrudes into recessed region 1020 of shaft 1012 a fixed distance and, in one embodiment, angles downwardly, or towards pericardium 1000. However, needle 1014 extends downwardly no further than depth, d, of cavity 1020. This prevents needle tip 1028 from snagging on tissue as device 902 is advanced to heart 900. Needle 1012 includes an access port 1030 in fluid communication with needle bore 1026. Access port 1030 is located near needle tip 1028 and is positioned within cavity 1020 of shaft 1012. Needle bore 1026 and access port 1030 are adapted for slidably receiving medical instruments, for example, guidewires, or fluids or gases. In one embodiment, needle 1014 extends from about 0.5 to about 3 mm into cavity 1020. In one embodiment, needle 1014 extends downwardly toward heart 900 at an angle of from about 15 to about 60 degrees with respect to a longitudinal access of shaft 1012.

Figure 10:
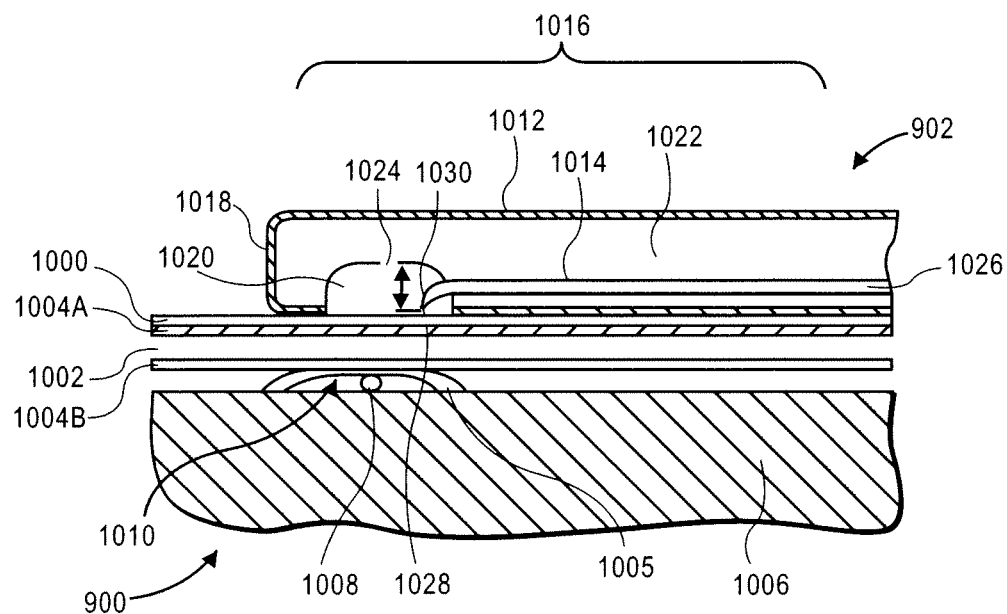
FIG. 10 schematically illustrates an epicardial access system in relation to the anatomic layers of the heart.

As illustrated in FIG. 10, suction lumen 1022 encompasses generally the entire interior of shaft 1012, and needle 1014 lies within suction lumen 1022. In other embodiments, shaft 1012 includes a secondary lumen separate from suction lumen 1022 for receiving needle 1014. Alternatively, needle 1014 may be integrally formed within shaft 1012.

In one embodiment, epicardial access device 902 may enter into the chest by, for example, a subxiphoid insertion route, and advance along a surface of heart 900 so that recessed region 1020 lies along fibrous layer 1000 adjacent a target blood vessel region. Alternatively, a sub-sternal or thoracascopic insertion route may be used in positioning device 902 along fibrous layer 1000. Suction or negative pressure is applied to suction port 1024 via suction lumen 1022, drawing fibrous layer 1000, visceral layer 1004A, epicardium 1004B and fat layer 1005 into recessed region 1020. The negative pressure is sufficient to cause the underlying fibrous layer 1000, visceral layer 1004A, epicardium 1004B and fat layer 1005 to engage the stationary and protruding needle tip 1028, such that needle tip 1028 penetrates the layers. Depth, d, of cavity 1020 is such that when fibrous layer 1000, visceral layer 1004A, epicardium 1004B and fat layer 1005 are drawn upwardly, needle tip 1028 penetrates through the layers and into peri-adventitial space 1010. Alternatively, only fibrous layer 1000 and visceral layer 1004A are drawn upwardly such that needle tip 1028 penetrates through the layers and into pericardial space 1002.

A fluid, such as saline or a treatment agent, may be delivered through access port 1030 and into peri-adventitial space 1010 to hydraulically dissect tissue planes within peri-adventitial space 1010.

In one embodiment, fluid volume, pressure and flow rate are controlled manually via a syringe. In another embodiment, fluid pressure is controlled by a pressurized reservoir, such as a pressurized IV bag. In another embodiment, flow rate may be controlled by an IV pump. In still further embodiments, the delivery device may have a pressure gauge or relief valve to aid in manual control or pressure.

In other embodiments, a delivery device may be introduced directly to the peri-adventitial space during a medical procedure wherein the heart is exposed. In this aspect, a direct delivery device may be introduced to the epicardium during, for example, cardiac surgery such as valve surgery or coronary bypass surgery. FIG. 11 schematically illustrates an embodiment of such a direct access system. In one embodiment, a delivery device 1100 is a syringe. In one embodiment, syringe 1100 may be any syringe assembly suitable for delivering a fluid substance to a vasculature of the heart. Syringe 1100 includes a plunger 1102 fitted to a barrel 1104, which includes a small aperture 1106 on one end. Needle 1108 extends from barrel 1104 and may be secured within aperture 1106. Needle 1108 may be made of materials including, for example, micropolymers, metals and metal alloys. Needle 1108 may have dimensions similar to the needles described in regard to FIG. 5. In some embodiments, needle 1108 may be a blunt tipped needle so as to prevent accidental perforation of a coronary artery or vein. Needle 1108 may be of a sufficient length to extend through the tissue and fat layers overlying the heart surface and into the peri-adventitial space surrounding the underlying vasculature as previously described in reference to FIG. 10. A representative needle 1108 length may be between about 3 mm and about 30 mm.

FIG. 12 schematically illustrates another embodiment of a syringe direct delivery device having a stop feature. Similar to the syringe of FIG. 11, syringe 1200 includes plunger 1102 fitted to barrel 1104 having a small aperture 1106 on one end. Needle 1108 extends from barrel 1104 and may be secured within aperture 1106. Syringe 1200 further includes a stop feature 1202 secured to needle 1108. Stop feature 1202 sets the penetration depth of needle 1108 within the tissue. In this aspect, stop feature 1202 lies at a distance from a tip 1110 of needle 1108 so that needle tip 1110 may be advanced through fibrous layer 1000, visceral layer 1004A, epicardium 1004B and fat layer 1005 and into peri-adventitial space 1010 surrounding blood vessel 1008 as illustrated in FIG. 12. Alternatively, needle tip 1110 is only advanced through fibrous layer 1000 and visceral layer 1004A such that needle tip 1110 penetrates through the layers and is positioned within pericardial space 1002. Syringe 1100 may include multiple needles, which may be used for delivery of the same or different substances simultaneously to peri-adventitial space 1010.

A volume of fluid, such as a treatment agent or saline solution, may be loaded into barrel 1104. Needle 1108 may be advanced through fibrous layer 1000, visceral layer 1004A, epicardium 1004B and fat layer 1005 adjacent a treatment site within peri-adventitial space 1010 so that a dispensing port of needle 1108 is within peri-adventitial space 1010. The fluid may then be delivered to peri-adventitial space 1010 at a pressure sufficient to hydraulically dissect the tissue planes. As previously discussed, a sufficient pressure, may be, for example, approximately 30 mmHg. The volume of fluid delivered may be, in one embodiment, between approximately 0.1 cc and 20 cc, preferably at least 1.0 cc. In an embodiment, where the fluid is saline or other biocompatible solution, the fluid is drained and then the treatment agent is delivered.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method comprising:
    advancing a catheter assembly within a lumen of a coronary blood vessel, the catheter assembly having a primary cannula attached at a distal end to a cylindrical housing, the cylindrical housing having a window formed through one side and a balloon formed around another side of the cylindrical housing, wherein the balloon extends around less than an entire circumference of the cylindrical housing and wherein the balloon is positioned between an outer surface of the cylindrical housing and a vessel wall of the coronary blood vessel such that when the balloon is inflated the balloon contacts a portion of the vessel wall adjacent the balloon and moves the one side of the cylindrical housing toward a portion of the vessel wall adjacent the window to press the window against the vessel wall;
    introducing a needle through the window to the vessel wall and into a treatment site within one of a peri-adventitial space or a pericardium adjacent the coronary blood vessel by advancing the needle through the window;
    delivering a first substance through the needle and out an end of the needle directly to the treatment site at a pressure sufficient to hydraulically dissect tissue planes within the peri-adventitial space or the pericardium adjacent the coronary blood vessel, wherein the first substance is delivered in an amount of at least 1.0 cc and the pressure sufficient to hydraulically dissect tissue planes is from about 30 mm Hg to about 150 mm Hg;
    withdrawing the first substance through the needle once the tissue planes are dissected; and
    delivering a second substance comprising a treatment agent through the needle and into the dissected tissue planes, and wherein an amount of the second substance is less than the amount of the first substance.

2. The method of claim 1 wherein at least 0.1 cc of the treatment agent is delivered through the needle.

3. The method of claim 1 wherein the needle is capable of one of subxyphoid, sub-sternal and thoracascopic access to the treatment site.

4. The method of claim 1 wherein between 0.1 cc and 20 cc of the treatment agent is introduced to the peri-adventitial space.

5. The method of claim 1 wherein the treatment agent is a drug selected from a group consisting of an HDL mimetic, an anti-inflammatory and an anti-proliferative.

6. The method of claim 1 wherein the treatment agent is a non-living biologic selected from a group consisting of extra cellular matrix, urinary bladder matrix, small intestinal submucosa and liver derived biomatrix.

7. The method of claim 1 wherein the treatment agent is a living biologic selected from a group consisting of bone marrow stem cells, mesenchymal cells and endothelial progenitor cells.

8. The method of claim 7 wherein the living biologic is composed of a mixture of a matrix gel and drug loaded particles.

9. The method of claim 1 wherein the treatment agent is composed of one of a nanoparticle and a microparticle.

10. The method of claim 9 wherein the one of the nanoparticle and the microparticle have an average diameter of about 15 microns or more.

11. The method of claim 1 wherein the treatment agent is composed of a gel.

* * * * *